United States Patent
Schmitz et al.

(10) Patent No.: US 6,610,320 B2
(45) Date of Patent: Aug. 26, 2003

(54) COMPOSITIONS AND METHODS FOR IMPROVING VASCULAR HEALTH

(75) Inventors: Harold H. Schmitz, Branchburg, NJ (US); Kati A. Chevaux, Seattle, WA (US); Amy Dombroski, Stanhope, NJ (US); Ralph Jerome, Blairstown, NJ (US)

(73) Assignee: Mars, Incorporated, McLean, VA (US)

( * ) Notice: Subject to any disclaimer, the term of this patent is extended or adjusted under 35 U.S.C. 154(b) by 12 days.

(21) Appl. No.: 09/829,782

(22) Filed: Apr. 10, 2001

(65) Prior Publication Data

US 2002/0018807 A1 Feb. 14, 2002

Related U.S. Application Data

(60) Provisional application No. 60/197,135, filed on Apr. 14, 2000.

(51) Int. Cl.$^7$ ................................. A61K 35/78
(52) U.S. Cl. ............... 424/440; 424/725; 424/742; 424/757; 424/777; 424/451
(58) Field of Search ............... 424/725, 757, 424/777, 400, 439, 440, 442, 451

(56) References Cited

U.S. PATENT DOCUMENTS

| | | | |
|---|---|---|---|
| 4,808,574 A | | 2/1989 | Brekhman et al. ............ 514/23 |
| 4,840,966 A | * | 6/1989 | Hara et al. |
| 4,883,788 A | * | 11/1989 | Day et al. |
| 5,244,887 A | | 9/1993 | Straub |
| 5,502,045 A | | 3/1996 | Mietten et al. |
| 5,554,645 A | | 9/1996 | Romanczyk, Jr. et al. |
| 5,607,965 A | | 3/1997 | Kondo et al. |
| 5,702,752 A | | 12/1997 | Gugger et al. ............ 426/634 |
| 5,892,068 A | | 4/1999 | Higgins, III |
| 5,932,562 A | | 8/1999 | Ostlund, Jr. |
| 5,952,374 A | | 9/1999 | Clarkson, Jr. et al. ...... 514/456 |
| 5,972,345 A | | 10/1999 | Chizick et al. .......... 424/195.1 |
| 6,013,771 A | | 1/2000 | Shen et al. ................. 530/378 |
| 6,025,348 A | | 2/2000 | Goto et al. |
| 6,087,353 A | | 7/2000 | Stewart et al. |
| 6,106,886 A | | 8/2000 | van Amerongen et al. |
| 6,136,349 A | * | 10/2000 | Karppanen et al. |
| 6,207,702 B1 | * | 3/2001 | Schmitz et al. |
| 6,228,993 B1 | | 5/2001 | Konwinski ................. 530/378 |
| 6,231,915 B1 | | 5/2001 | van Amerongen et al. |
| 6,242,001 B1 | | 6/2001 | Bruce et al. |
| 6,312,753 B1 | * | 11/2001 | Kealey et al. |
| 6,313,273 B1 | | 11/2001 | Thomas et al. ............. 530/378 |
| 2002/0018807 A1 | | 2/2002 | Schmitz et al. |
| 2002/0039619 A1 | | 4/2002 | Monagle |

FOREIGN PATENT DOCUMENTS

| | | |
|---|---|---|
| CA | 1099627 | 3/1995 |
| CN | 1 099 627 | 3/1995 |
| DE | 4102054 | 7/1992 |
| EP | 0 097 671 A1 | 2/1999 |
| EP | 0943245 | 9/1999 |
| EP | 1046 396 | 10/2000 |
| EP | 1 074 185 A1 | 2/2001 |
| JP | 09291039 A * | 11/1997 |
| WO | WO 97/36497 | 10/1997 |
| WO | WO 97/37547 | 10/1997 |
| WO | WO 98/06405 | 2/1998 |
| WO | WO 98/13023 | 4/1998 |
| WO | WO 98/33494 | 8/1998 |
| WO | WO 98/58554 | 12/1998 |
| WO | WO 99/11144 | 3/1999 |
| WO | WO 99/15546 | 4/1999 |
| WO | WO 99/15547 | 4/1999 |
| WO | 99/30569 | 6/1999 |
| WO | WO 99/32097 | 7/1999 |
| WO | WO 99/43218 | 9/1999 |
| WO | WO 99 48386 | 9/1999 |
| WO | 99/48386 | 9/1999 |
| WO | WO 99/53925 | 10/1999 |
| WO | WO 99/56729 | 11/1999 |
| WO | WO 99/59421 | 11/1999 |
| WO | WO 99/63841 | 12/1999 |
| WO | WO 00/00043 | 1/2000 |
| WO | WO 00/15201 | 3/2000 |
| WO | WO 00/24266 | 5/2000 |
| WO | WO 00/27219 | 5/2000 |
| WO | WO 00/30663 | 6/2000 |
| WO | WO 00/30664 | 6/2000 |
| WO | WO 00/30665 | 6/2000 |
| WO | WO 00/62774 | 10/2000 |
| WO | WO 01/06866 | 2/2001 |
| WO | WO 01/26668 | 4/2001 |
| WO | WO 01/37781 | 5/2001 |
| WO | WO 01/49285 | 7/2001 |
| WO | WO 01/51088 | 7/2001 |

OTHER PUBLICATIONS

CAN Healthy–Chocolate,0344 Researchers Test Cholesterol– lowering Chocolates, The Associated Press, Oct. 31, 1999.

Nicholas J. Jardine, Chapter 8, Phytochemicals and Phenolics, Chocolate and Cocoa, Health and Nutrition, Edited by Ian Knight (Knight International), pp. 119–142.

J. Wegrowski, et al., The Effect of Procyanidolic Oligomers on the Composition of Normal and Hypercholesterolemic Rabbit Aortas, Biochemical Pharmacology, 33:3491–3497, 1984.

T.T. Yang and M.W.L. Koo, Hypocholesterolemic Effects of Chinese Tea, Pharmacological Research, 35:505–512, 1997.

(List continued on next page.)

Primary Examiner—Leon B. Lankford, Jr.
Assistant Examiner—Ruth Davis
(74) Attorney, Agent, or Firm—Nada Jain, P.C.; Nada Jain

(57) ABSTRACT

This invention relates to compositions containing polyphenols, for example, cocoa polyphenols such as procyanidins, in combination with at least one cholesterol lowering agent, and methods for improving vascular health including treating and preventing atherosclerosis and cardiovascular disease.

17 Claims, 8 Drawing Sheets

OTHER PUBLICATIONS

Hans M.G. Princen, et al., No Effects of Consumption of Green and Black Tea on Plasma Lipid and Antioxidant Levels and on LDL Oxidation in Smokers, Arterioscler Thromb Vasc Biol., 18:833–841, 1998.

Ping Tim Chan, et al., Jasmine Green Tea Epicatechins are Hypolipidemic in Hamsters (*Mesocricetus auratus*) Fed a High Fat Diet, The Journal of Nutrition, 129:1094–1101.

Russell Ross, Ph.D., Atherosclerosis—An Inflammatory Disease, The New England Journal of Medicine, 340:115–126, 1999.

Malcolm Law, Plant Sterol and Stanol Margarines and Health, BMJ, 320:861–864, 2000.

International Search Report/PCT US 01/11542.

* cited by examiner

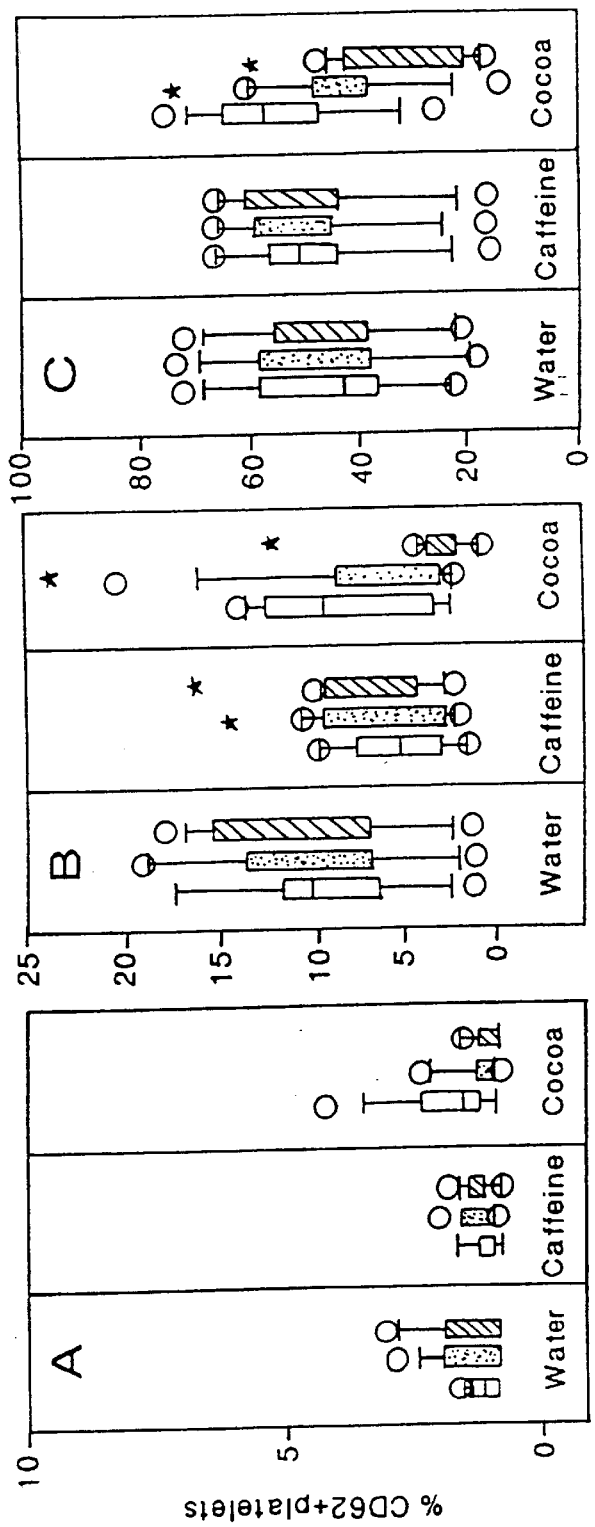

FIG. 4

Effect of cocoa beverage consumption on platelet surface expression of activated GP11b-111a with and without simulation with weak agonisys. Platelet activation marker expression is presented as Tukey box plots at times zero (white boxes), 2 hours (light grey boxes), and 6 hours (dark grey boxes) post consumption of water, a caffeine-containing control beverage (caffeine) or a cocoa beverage (cocoa). (A) percentage of platelets expressing activated gp11b-111a (PAC1= platelets) without stimulation (B) after stimulation with epinephrine (20uM) or (C) with ADP (20uM). Activated GP11b-111a is expressed on the surface of activated platelets. Each box shows the 25-75th percentile, the horizontal bar in the box shows the median.. The lines outside the box show the 10th and 90th percentile. Asterisks indicate P 0.05 between zero time and 6 hour hour time points of each respective data set repeated measure ANOVA on ranks, Student-Newman-Keuls multiple comparison method, n=10 in each

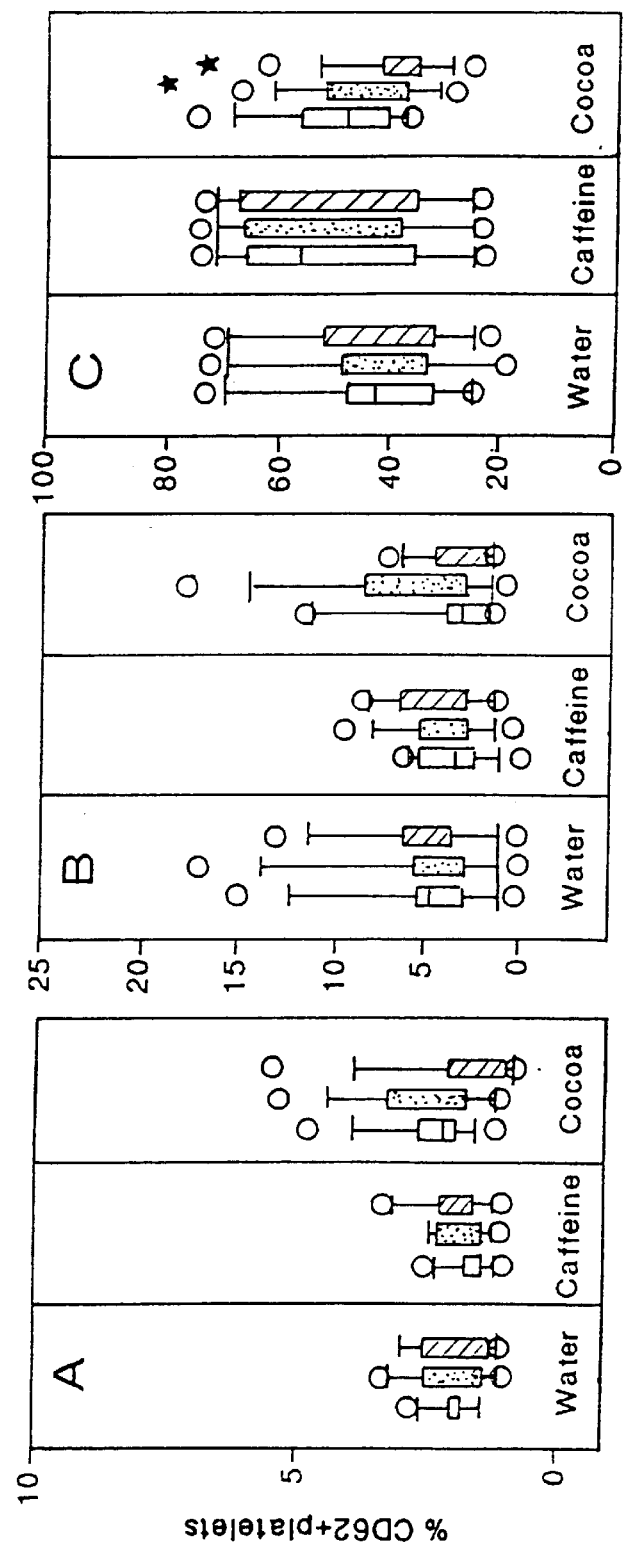

FIG. 5

Effect of cocoa beverage consumption on platelet surface surface expression of activated P-selection with and without stimulation with weak agonists. platelet activation marker expression presented as Tukey box plots at times zero (white boxes), 2 hours (light grey boxes) and 6 hours (dark grey boxes) post-consumption of water, a caffeine-containing control beverage (caffeine) or a cocoa beverage (cocoa).(A) Percentage of platelets expressing P-selection(CD62P+platelets) without stimulation, (P) after stimulation with epinephrine (20uM) or (C) with ADP(20uM). P-selection is expressed on the surface of activated Asterisks indicate P<0.05 between zero time and 2 hours and between zero time and six

COMPOSITIONS AND METHODS FOR IMPROVING VASCULAR HEALTH

This application claims priority, under 35 U.S.C. §119, from the U.S. provisional patent application Ser. No. 60/197,135, filed Apr. 14, 2000, the disclosure of which is hereby incorporated herein by reference.

FIELD OF THE INVENTION

This invention relates to compositions containing polyphenols, for example, cocoa polyphenols such as procyanidins in combination with at least one cholesterol lowering agent and methods for improving vascular health including treating and preventing atherosclerosis and cardiovascular disease.

BACKGROUND OF THE INVENTION

Coronary artery disease, the primary form of cardiovascular disease (CVD), is the major cause of death in the United States today. Cerebrovascular disease is the third. The etiology of both coronary artery and cerebrovascular diseases is attributed to atherosclerosis. Through its clinical manifestations, atherosclerosis is the major cause of the more than one million heart attacks, approximately 400,000 strokes that occur each year and numerous vascular circulation problems. Many patients suffer from hypertension.

A substantial body of evidence has established a causal relationship between hypercholesterolemia and premature atherosclerosis; the higher the levels of plasma cholesterol, the greater the risk of subsequent heart attack. (see e.g. Steinberg, D., JAMA 264:3047 (1990)). In the chain of events leading to atherosclerosis, it is believed that the initiating event is the formation of "fatty streaks" in carotid, coronary, and cerebral arteries, and in the aorta. These lesions include fatty deposits of cholesterol and cholesteryl ester that are found principally within the smooth muscle cells and macrophages of the intimal layer. The migration and proliferation of vascular smooth muscle cells play a crucial role in the pathogenesis of atherosclerosis following the initial deposition of lipid.

Additionally, the development of atheroslerosis and cardiovascular disease are modulated by, and/or associated with, LDL oxidation, cyclo-oxygenase (COX) activity, lipoxygenase (LOX) activity, nitric oxide (NO) production, and nitric oxide synthase (NOS) activity. The relationships among the various pathways and processes involved herewith are represented in FIG. 1 and are described in detail in the International Appl. No. PCT/US97/05693 published as WO 97/36497, the relevant portions of which are hereby incorporated herein by reference. Briefly, LDL oxidation is a critical step in the initiation of lesions (atheromas) which occur when macrophages take up oxidatively modified LDL and transform into so-called "foam cells." Enzymes COX and LOX are involved in arachidonic acid pathway which leads to the production of prostaglandins and thromboxane A2, the latter being known to cause vasoconstriction and platelet aggregation, and thus progression of atherosclerosis. Nitric oxide is known to inhibit platelet aggregation, monocyte adhesion/chemotaxis and proliferation of vascular smooth muscle all of which are considered to be responsible for progression of atherosclerosis. Cocoa polyphenols have been shown to have beneficial effects on the above-described processes by inhibiting LDL oxidation, enhancing NO/NOS activity and inhibiting COX/LOX activity. These effects are shown, for example, in the International Appl. No. PCT/US97/05693 published as WO97/36497 and the examples reported in the application. Cocoa polyphenols can be used to treat or prevent conditions which are known to be affected by the administration of non-steroidal anti-inflammatory drugs, for example, aspirin.

Despite the benefits of the cocoa polyphenol on the number of pathways and conditions associated with induction and progression of atherosclerosis and CHD, it has been found that these compounds do not have noticeable cholesterol lowering effect. Thus, the inventors have prepared an improved composition containing polyphenols in combination with at least one cholesterol lowering agent. The composition has enhanced effects on vascular health of a mammal, particularly a human, in comparison to the previously known compositions containing polyphenol or cholesterol lowering agents.

SUMMARY OF THE INVENTION

The invention relates to compositions and methods for improving vascular health in a mammal, a human or a veterinary animal in particular.

In one aspect, the invention relates to a composition, such as a food, a food additive, a dietary supplement, or a pharmaceutical comprising a cocoa polyphenol and a cholesterol lowering agent. The composition may optionally contain L-arginine.

In another embodiment, the invention relates to a cholesterol reducing confectionery, most preferably cholesterol reducing chocolates (e.g. dark chocolate) and confectionery containing cholesterol reducing chocolate.

In another aspect, the invention relates to a method for improving vascular health, including preventing or treating atherosclerosis and cardiovascular disease in a mammal, such as a human or a veterinary animal, by administering a composition containing a cocoa polyphenol and a cholesterol-reducing compound, and optionally L-arginine. Polyphenols from other sources having properties similar to those of cocoa polyphenols may also be used in the compositions and methods of the invention in combination with cholesterol lowering agents, such as sterol and/or stanol based cholesterol lowering agents.

In yet another embodiments, the invention relates to a method of enhancing absorption of a polyphenol, for example a flavanol or a flavonol by administering to a mammal the polyphenol in combination with a phytosterol and/or phytostanol. The compositions and products of manufacture for use in the method are also provided.

BRIEF DESCRIPTION OF THE DRAWINGS

FIGS. 4A–C shows the effect of cocoa beverage consumption on platelet surface expression of activated GPIIb-IIIa with and without stimulation with weak agonists.

FIGS. 5A–C shows the effect of cocoa beverage consumption on platelet surface expression of activated P-selectin with and without stimulation with weak agonists.

DETAILED DESCRIPTION

Figure 1:
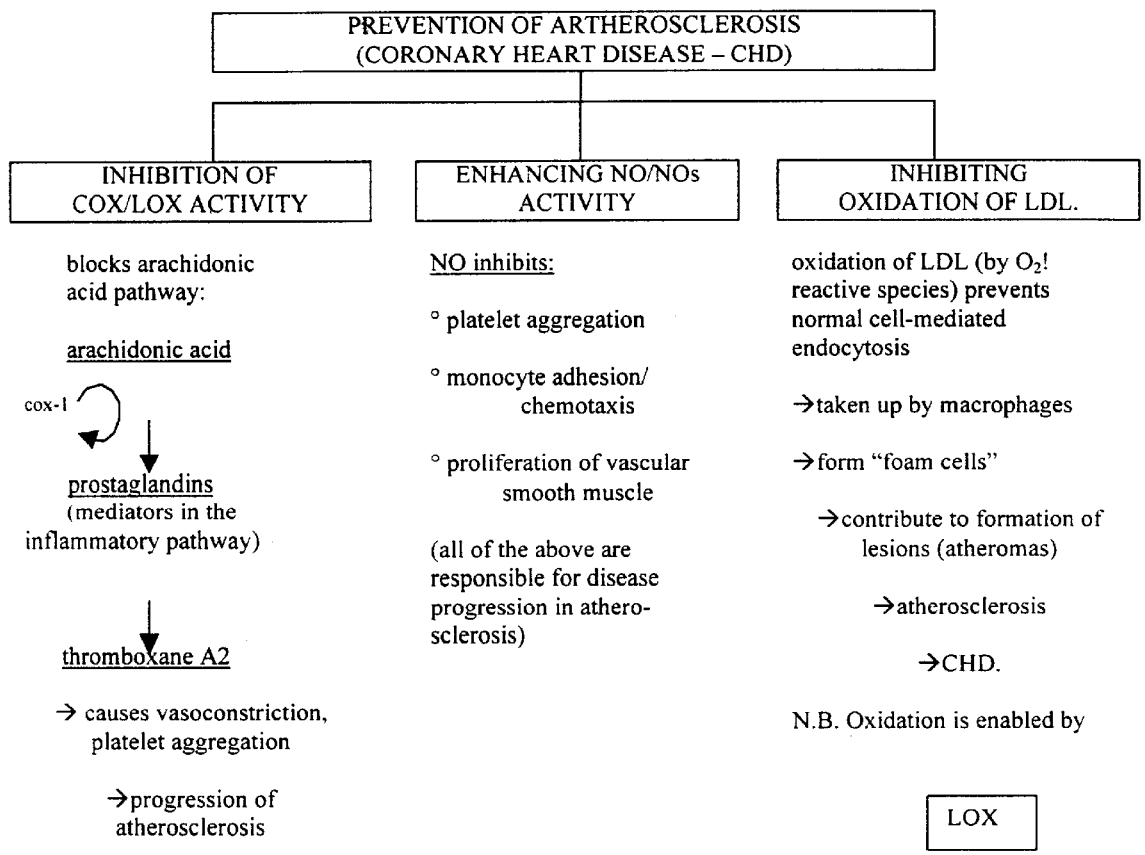
FIG. 1 is a chart representing major contributing factors to the progression of coronary heart disease (CHD) and showing how cocoa polyphenols contribute to the prevention of the progression of the disease.
Figure 2A:
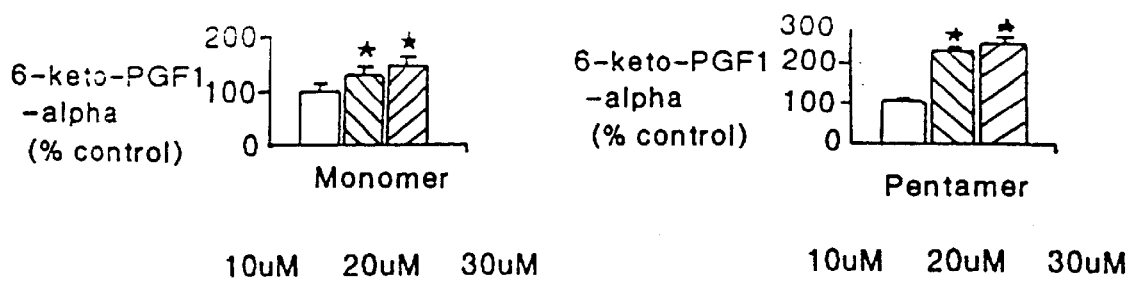
FIGS. 2A–D show the effect of phytochemicals on basal endothelial cell synthesis of the prostanoids and endothelins in BAECS. (*=significantly different from control at p<0.05)
Figure 2B:
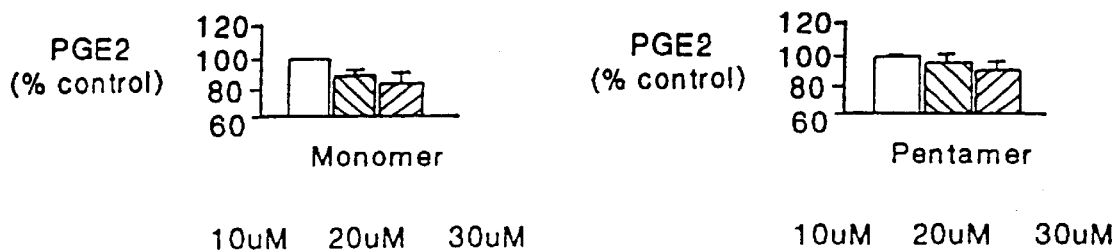
Figure 2C:
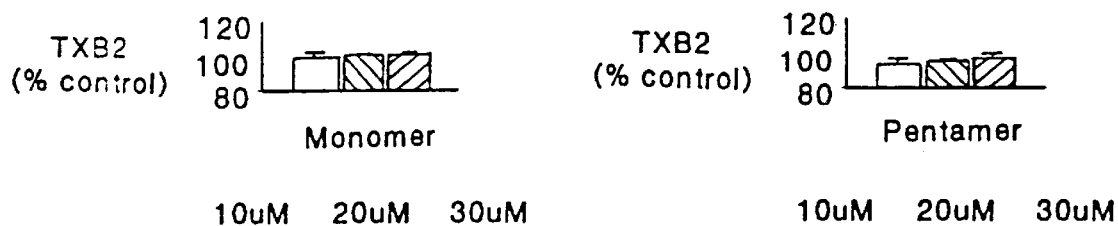
Figure 2D:
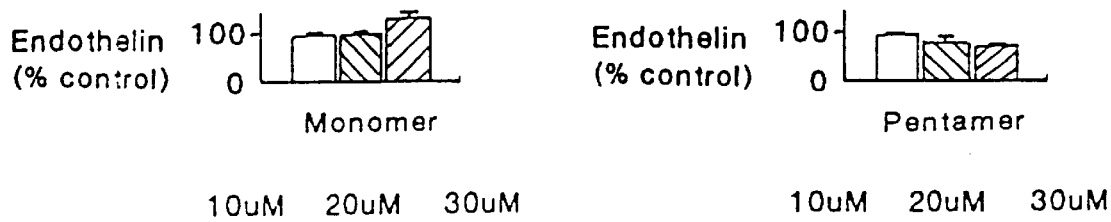

All patents, patent applications and references cited in this application are hereby incorporated herein by reference. In case of any inconsistency, the present disclosure governs.

The present invention relates to a composition containing a cocoa polyphenol in combination with a cholesterol lowering agent, for example, a sterol and/or stanol based cholesterol lowering agent, which composition is useful for improving or promoting vascular health in a mammal. The composition may optionally contain L-arginine, calcium, potassium, magnesium, vitamin E, vitamin C, any of the vitamins of the B complex, a carotenoid, guar gum, or a mono or polyunsaturated fatty acid (e.g. omega-3 fatty acid). Compositions containing polyphenols from other sources having properties similar to those of cocoa polyphenols may also be used in the compositions and methods of the invention in combination with cholesterol lowering agents, for example, sterol and/or stanol based cholesterol lowering agents, are also within the scope of the invention.

As used herein, the term "cocoa polyphenol" (CP) refers to a polyphenolic substance including proanthocyanidin, more particularly procyanidin, present in cocoa beans or extracted from cocoa beans or cocoa ingredients. The term "procyanidin" includes both the monomers and the oligomers of catechin and epicatechin. Any reference to cocoa polyphenol herein should be understood to also apply to cocoa procyanidin. The term "cocoa ingredient" refers to a cocoa solids-containing material derived from shell-free cocoa nibs such as chocolate liquor and partially or fully-defatted cocoa solids (e.g. cake or powder). The phrase "cholesterol lowering agent" means any compound, combination of compounds, an extract or a plant component, naturally found or processed, that has the property of lowering cholesterol levels in a mammal when administered in an effective amount. When such cholesterol lowering agent is a compound or a combination of compounds that is of a sterol or stanol type, i.e., including derivatives and isomeric forms, the cholesterol lowering agent is referred to as a "sterol and/or stanol based cholesterol lowering agent." When the phrase is used in reference to a composition, for example, "a cholesterol reducing dark chocolate," it means that the composition has the property of lowering cholesterol. As a person of skill in the art can understand from the usage herein, the term "vascular" refers to the entire vascular system, i.e., it encompasses the heart, and the term "vascular health" is inclusive of the cardiovascular health and/or coronary health. "Promoting vascular health" refers to achieving the beneficial health effects described herein.

The cocoa polyphenols may be of natural origin, i.e., derived from a cocoa bean, or prepared synthetically. A person of skill in the art may select natural or synthetic cocoa polyphenol based on availability or cost. Cocoa polyphenols may be included in the composition as a cocoa ingredient containing cocoa polyphenols, for example, a chocolate liquor in chocolate, or may be added independently of cocoa ingredients, for example, as an extract, extract fraction, pooled extract fractions or a synthetically prepared compound. The cocoa polyphenols include cocoa procyanidins, which may be monomers and/or oligomers of epicatechin and catechin. Procyanidin monomers include (+)-catechin, (−)-epicatechin and their respective epimers (e.g. (−)-catechin and (+)-epicatechin) and have the structure:

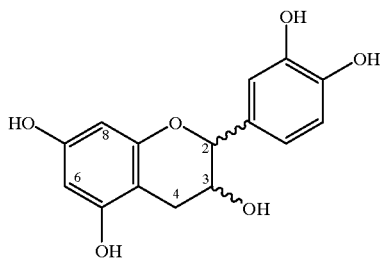

The procyanidin oligomers may have from 2 to about 18, preferably from 2 to about 12, and most preferably from 2 to about 10 monomeric units. For example, oligomers may be dimers, trimers, tetramers, pentamers, hexamers, septamers, octamers, nonamers and decamers. In the oligomer, monomers are connected via interflavan linkages of (4→6) and/or (4→8). Oligomers with exclusively (4→8) linkages are linear; while the presence of at least one (4→6) bond results in a branched oligomer.

The cocoa polyphenol may be prepared by extraction from cocoa beans, cocoa nibs, or cocoa ingredients such as chocolate liquor, partially defatted cocoa solids, and/or fully defatted cocoa solids. Preferably, the extract is prepared from a fully or partially defatted cocoa powder. Beans from any species of Theobroma, Herrania or inter- and intra-species crosses thereof may be used. The extract may be prepared from fermented, underfermented or unfermented beans, the fermented beans having the least amount of cocoa polyphenols and the unfermented the most. The selection of beans may be made based on the fermentation factor of the beans, for example, the extract may be made from the beans having a fermentation factor of 275 or less. Optimizing the level of polyphenols in the cocoa ingredient and extract thereof by manipulating the degree of fermentation may be done as described in the International Appl. No. PCT/US97/15893 published as WO98/09533, the relevant portions of which are hereby incorporated herein by reference.

Cocoa polyphenols may be extracted from cocoa ingredients that have been processed using traditional methods of cocoa processing (described, for example, in Industrial Chocolate Manufacture and Use, ed. Beckett, S. T., Blackie Acad. & Professional, New York, 1997, such as in Chapters 1, 5 and 6) or using an improved processing method described in U.S. Pat. No. 6,015,913 to Kealey et al. that preserves polyphenols (by preventing their destruction) in cocoa ingredients in contrast to the traditional methods. The improved cocoa processing method omits the traditional roasting step. Thus, cocoa ingredients obtainable by (a) heating the cocoa bean for a time and a temperature sufficient to loosen the cocoa shell without roasting the cocoa nib; (b) winnowing the cocoa nib from the cocoa shell; (c) screw pressing the cocoa nib and (d) recovering the cocoa butter and partially defatted cocoa solids which contain preserved levels of cocoa polyphenols, may be used. The method retains a much higher level of higher procyanidin oligomers than traditionally. Cocoa solids produced by this method may contain greater than 20,000 μg of total procyanidins per gram nonfat solids; preferably greater than 25,000 μg/g, more preferably greater than 28,000 μg/g, and most preferably greater than 30,000 μg/g. For purposes of this invention, the total procyanidin amounts are determined as described in Example 3.

Cocoa polyphenols may be extracted from the sources indicated above using solvents in which the polyphenols dissolve. Suitable solvents include water or organic solvent such as methanol, ethanol, acetone, isopropyl alcohol and ethyl acetate. Solvent mixtures may also be used. When water is used as the solvent, it is preferable that it is slightly acidified, for example with acetic acid. Preferred solvents are mixtures of water and organic solvent, for example aqueous methanol, ethanol or acetone. Aqueous organic solvents may contain, for example, from about 50% to about 95% of organic solvent. Thus, 50%, 60%, 70%, 80% and 90% organic solvent in water may be used. The solvent may also contain a small amount of acid such as acetic acid, for example, in the amount of about 0.5% to about 1.0%. The composition of the extracts, i.e., the representation (i.e., oligomeric profile) and the amount of procyanidin oligomers, will depend on the choice of solvents. For example, the water extract contains primarily monomers, the ethyl acetate extract contains monomers and lower oligomers, mainly dimers and trimers, and the aqueous methanol, ethanol or acetone extract contains monomers and a range of higher oligomers. One of the preferred solvents for extraction of monomer as well as higher procyanidin oligomers is 70% acetone. However, any extract containing polyphenols is useful in the invention. The methods of cocoa polyphenol extraction are known in the art and are described, for example, in the U.S. Pat. No. 5,554,645 to Romanczyk et al. and the International Appl. No. PCT/US97/05693, published as WO97/36497. Thus, in one embodiment, the cocoa extract is prepared by reducing cocoa beans to cocoa powder, defatting the powder, extracting the cocoa polyphenols, and purifying the extract. The cocoa powder can be prepared by freeze-drying the cocoa beans and pulp, depulping and dehulling the freeze-dried cocoa beans, and grinding the dehulled beans.

The cocoa polyphenol extract may be purified, for example, by removal of the caffeine and/or theobromine, and further purified by gel permeation chromatography and/or High Pressure Liquid Chromatography (HPLC). Gel permeation chromatography (e.g. on Sephadex LH-20) may be used to enrich the extract for higher procyanidin oligomers. For example, the eluate containing monomers and lower oligomers may not be collected until the oligomer(s) of choice begins eluting from the column. An example of such an extract is known in the art and is described in Example 5 of the International Appl. No. PCT/US97/05693, published as WO97/36497, the relevant portions of which are hereby incorporated by reference herein. By using preparative HPLC, for example, normal phase HPLC, the extract may be fractionated, for example, into monomeric and oligomeric fractions containing at least 50% by weight of the monomer or specific oligomer(s). When the fractions contain the monomers and lower oligomers (up to and including the tetramer), the fractions contain about 90 to 95% by weight of the particular oligomeric fraction. The desired fractions may be pooled after separation to obtain a combination of oligomers of choice for example to contain oligomers 3–10 or 5–10. A person of skill in the art can manipulate the chromatographic conditions to achieve the desired procyanidin profile in view of the guidance in this specification, general knowledge in the art and, for example, the teachings of U.S. Pat. No. 5,554,645 to Romanczyk et al. and the International Appl. No. PCT/US97/05693, published as WO97/36497.

Cocoa polyphenol may also be provided in the composition of the invention by cocoa ingredients containing polyphenols or by including chocolate, which may be milk, sweet and semi-sweet, and is preferably dark chocolate, and low fat chocolate. The cocoa ingredients may be prepared using traditional cocoa processing procedures but is preferably prepared using the method described in U.S. Pat. No. 6,015,913 to Kealey et al. Alternatively, to enhance the level of cocoa polyphenols, chocolate liquor and cocoa solids prepared from cocoa beans having a fermentation factor of 275 or less may be used. These ingredients have cocoa polyphenol content that is higher than can be obtained using traditional cocoa processing methods (e.g. with roasting) and fully fermented beans. The chocolate may be prepared using conventional techniques from the ingredients described above or using an improved process for preserving cocoa polyphenols during chocolate manufacturing as described in the International Appl. No. PCT/US99/05414 published as WO99/45788, the relevant portions of which are hereby incorporated herein by reference. A chocolate prepared by at least one of the following non-traditional processes is referred to herein as a "chocolate having a conserved amount of cocoa polyphenols": (i) preparing cocoa ingredients from underfermented or unfermented cocoa beans; (ii) preserving cocoa polyphenol during cocoa ingredient manufacturing process; and (iii) preserving cocoa polyphenol during chocolate manufacturing process.

Synthetic procyanidins may also be used and are prepared by methods known in the art and as described for example in the International Appl. No. PCT/US98/21392 published as WO99/19319, the relevant portions of which are hereby incorporated herein by reference. Cocoa polyphenol derivatives may also be useful. These include gallated monomers and oligomers, glycosylated monomers and oligomers, and mixtures thereof; metabolites of the procyanidin monomers and oligomers, such as the sulphated, glucoronidated, and methylated forms; and enzyme cleavage products of procyanidins generated by colonic microflora metabolism or internal mammalian metabolism. The derivatives may be from natural sources or prepared synthetically.

The composition further comprises a cholesterol lowering agent. Any cholesterol lowering agent irrespective of its mode of action may be used. Suitable agents may act by reducing cholesterol absorption in the bile of a mammal or by reducing cholesterol synthesis. Examples of suitable agents are phytosterols, phytostanols and their derivatives and isomers; soy protein; soluble fibers, e.g. beta-glucan from, for example, oat and psyllium, nuts, rice bran oil, each of which is particularly suitable for use in food, dietary supplements and food additive compositions. Known cholesterol reducing drugs may also be used but are less preferred for use in the food and food additive compositions, but may be used in a pharmaceutical. It will be obvious to a person of skill in the art that the choice of the cholesterol lowering agent depends on the intended delivery vehicle (e.g. food, supplement, pharmaceutical) and the mode of administration. Thus, an agent that reduces absorption of cholesterol in the bile will not be preferred for intravenous administration. Similarly, if the delivery vehicle is food, a cholesterol lowering agent having a strong medicinal taste or smell may not be desirable.

Phytosterols are plant sterols that do not dissolve in water and have the molecular weight and the structure similar to cholesterol. Phytosterol reduce cholesterol absorption in the bile (of both endogenic and dietary cholesterol) as well as serum cholesterol levels (total and LDL) without being absorbed themselves. Over fourty plant sterols have been identified but beta-sitosterol, campesterol and stigmasterol are most abundant. Other examples of useful sterols are brassicasterol, desmosterol, chalinosterol, poriferasterol, an clionasterol. Individual sterols or a mixture of sterols, isolated from natural sources or synthetic, and isomers and derivatives thereof may be used. Particularly useful are saturated derivatives of sterols, known as stanols, in which all carbon-carbon bonds in the rings are saturated. Suitable stanols have 28 or 29 carbon atoms and include beta-sitostanol, clionastanol, 22,23-dyhydrobrassicastanol and campestenol. Phytosterols may be solid (e.g. powder, granules) or liquid (e.g. oil) form.

The sterols and stanols are found in several plant materials as described for example in the International Appl. No. PCT/EP96/02344. Exemplary sources of sterols/stanols are pine bark, soy oil, tall oil, bamboo shoot extract (described in the International Appl. No. PCT/US98/12556, published as WO98/57545), cocoa hulls and oil, and rice bran oil. Tall oil, a byproduct of the pulp and paper industry, is a good source of stanol, i.e., beta-stanol.

Plant sterol may be obtained from natural sources such as vegetative oils, vegetative oil sludge, vegetative oil distillates, and other plant oil sources such as tall oil by relatively simple and inexpensive means. For example, a preparation of sterols from vegetable oil sludge by using solvents such as methanol is described in U.S. Pat. No. 4,420,427 to Hamunen. Stanols are found in small amounts in nature but may be easily prepared from sterols by hydrogenating sterols by any of the several methods known to those of skill in the art. When a sterol starting material is prepared from a plant material it will contain a mixture of several different sterols thus, after hydrogenation, the resulting stanol will also be a mixture of different stanols. The mixtures are suitable for use in the present invention. However, pure specific sterol preparations may be hydrogenated as well to produce pure stanols that can also be utilized.

Cocoa oil extracted from cocoa hulls is a good source of phytosterol. Cocoa phytosterols are a mixture of free and bound sterols, with the free sterols being up to about 90% of the phytosterols present. The phytosterols include campesterol, β-sitosterol, stigmasterol, cycloartenoyl, 24-methylene cycloartenoyl, as well as minor amounts of other phytosterols. The bound phytoserols include the fatty acid esters or ferulate derivatives of the phytosterols. The cocoa oil also contains tocols, which include tocopherols (which have antioxidant properties) and tocotrienols (which may have cholesterol lowering activity. The cocoa oil is prepared by the process comprising the steps of: (i) grinding the cocoa hulls; (ii) extracting the ground cocoa hulls with a solvent for the phytosterols; (iii) removing the solvent; and (iv) recovering the cocoa oil. The cocoa hulls, a byproduct of the cocoa bean roasting, can be from dried fermented cocoa beans, micronized cocoa beans, roasted cocoa beans, and preferably from dried unfermented beans, which contain the highest total sterol content. The preferred cocoa beans are from *Theobroma cacao*. The preferred solvents are petroleum ether, hexane, pentane, and ethyl ether. The solvent may be recovered by vacuum distillation. In one embodiment, freeze dried hulls are ground to a fine powder with a Tekmar Mill (Cincinatti, Ohio) and the ground mass is subjected to an overnight extraction with redistilled petroleum ether (b. p. 38–39.6° C.) in a Soxtec apparatus (Fisher Scientific, Springfield, N.J.). The following morning, the solvent is carefully removed by slow evaporation under a stream of nitrogen, and the resultant extracts is stored at −40° C. The phytosterols may then be purified by preparative HPLC or column chromatography.

Esterified forms of both sterols and stanols may also be used. Esterification renders the sterols/stanols more soluble in fats and oils, which may, in some instances, help their incorporation into food products or other delivery vehicles. For example, sterols may be esterified with fatty acid esters. Examples of such esterified sterols include sitosterol acetate, sitosterol oleate and stigmasterol oleate. Stanol esters may be prepared as is known in the art and for example as described in U.S. Pat. No. 6,031,118 to van Amerongen et al., U.S. Pat. No. 5,892,068 to Higgins, U.S. Pat. No. 5,502,045 to Miettenen et al, and the International Appl. No. PCT/CA99/00655 (published as WO00/04887). In one embodiment, useful stanol esters are prepared by esterifying at least one sterol with a $C_2$ to $C_{22}$ fatty acid ester as described in U.S. Pat. No. 5,958,913 to Miettenen et al. Other methods known in the art may be used to increase the solubility of sterols/stanols upon administration to a mammal. One such method is described in U.S. Pat. No. 5,932,562 to Ostlund, wherein the sterol/stanol is mixed with lecithin to obtain a water soluble powder.

Sterols/stanols may be added to the composition in powder form by mixing with other ingredients. In case of a food composition, stanol/sterols as well as other cholesterol lowering agents are conveniently added at the step of mixing. During the preparation of cholesterol lowering chocolate, for example, sterols/stanols may be added to the dry mix containing sugar, the melting butter; the nibs before milling; or the melted chocolate, which may be less preferred. To facilitate mixing, sterols/stanols may be first dissolved in a solubilizing agent such as fat, vegetable oil, monoglycerides, diglycerides, triglycerides, tocopherols and mixtures thereof. Effective carriers for making suspensions and emulsions of sterols/stanols are water, alcohol, polyol, other edible compounds, for example chocolate liquor, in which sterols/stanols are at least partially soluble and mixtures thereof.

Soy protein may be added to the composition in any known form, for example, it may be soy protein isolate, soy protein concentrate, textured soy protein or soy flour, flakes and grits. Whole grain or fragment thereof may also be used as described, for example, in Example 5. Various forms of soy protein are well known in the art and are commercially available. Its properties and methods of obtaining are described, for example, in Soy Protein and Human Nutrition, Wilcke et al., eds., Acad. Press, NY, 1979. Soy protein may be used in combination with any sterol and/or stanol based cholesterol lowering agent.

Soluble plant fibers, e.g. beta-glucan, are capable of reducing plasma cholesterol. The fibers for use in the present invention may be obtained from any source of beta-glucan, preferably oat grain and oat bran. The fibers may be prepared and added to compositions according to methods known in the art. They are particularly suitable for orally delivered compositions such as foods and dietary supplements. Beta-glucan and other soluble plant fibers may be used in combination with any sterol and/or stanol based cholesterol lowering agent.

The composition of the invention may also contain L-arginine, which may be provided in the composition of the invention in various forms, for example as a purified compound, an extract from an L-arginine containing plant, or in the form of a seed/nut ingredient, e.g. nut flour, or as an entire seed/nut. Any L-arginine source may be used, synthetic or natural. Preferred L-arginine sources are soy beans and nut meats such as peanuts, walnuts, almonds, and hezelnuts. Defatted and partially defatted nut meats may be used. These may be ground and are referred to as nut flour.

The composition may also contain calcium, potassium, magnesium, vitamin E, vitamin C, any of the vitamins of the B complex, a carotenoid, guar gum, or a mono or polyunsaturated fatty acid (e.g. omega-3 fatty acid), which can be obtained according to the methods known in the art. The mono or polyunsaturated fatty acids may be used in the form of an olive oil, fish oil or a nut. Examples of nuts suitable for this use are: peanuts, almonds and walnuts.

A composition comprising a polyphenol having at least one of the following properties: inducing vasorelaxation, inhibiting COX activity, inhibiting LOX activity, inhibiting oxidation of LDL, enhancing NOS activity, increasing the level of NO, inhibiting platelet aggregation, monocyte adhesion and proliferation of vascular smooth muscle, reducing blood pressure, reducing thrombosis, and modulating oxidative stress, and a cholesterol lowering agent are also within the scope of the invention. Any cholesterol lowering agent, for example, a sterol and/or stanol based cholesterol lowering agent, may be used. In such a composition, the sterol and/or stanol based cholesterol lowering agent enhances the bioavailability of the polyphenol. Examples of such polyphenols are flavanols (e.g. catechin, epicatechin and gallated derivatives thereof), flavonol (e.g. quercetin, kaempserol, myricetin and their glycosylated derivatives), and procyanidins (e.g. procyanidin dimer, which may be from cocoa).

The composition of the invention is useful as a food, a food additive, a dietary supplement, or a pharmaceutical. The compositions may contain a carrier, a diluent, or an excepient. Depending on the intended use, the carrier, diluent, or excepient may be chosen to be suitable for human or veterinary use, food, additive, supplement or pharmaceutical use.

As used herein a "food" is a material consisting essentially of protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993. The term food includes a beverage adapted for human or animal consumption. As used herein a "food additive" is as defined by the FDA in 21 C.F.R. 170.3(e)(1) and includes direct and indirect additives. As used herein, a "pharmaceutical" is a medicinal drug. See Merriam-Webster's Collegiate Dictionary, 10th Edition, 1993. A pharmaceutical may also be referred to as a medicament. As used herein, a "dietary supplement" is a product (other than tobacco) that is intended to supplement the diet that bears or contains the one or more of the following dietary ingredients: a vitamin, a mineral, an herb or other botanical, an amino acid, a dietary substance for use by man to supplement the diet by increasing the total daily intake, or a concentrate, metabolite, constituent, extract or combination of these ingredients.

Any conventional food including any beverage which has been improved by cholesterol lowering agent in combination with a polyphenol such as a cocoa polyphenol or a derivative thereof, and optionally in combination with L-arginine, calcium, potassium, magnesium, vitamin E, vitamin C, any of the vitamins of the B complex, a carotenoid, guar gum, and/or a mono or polyunsaturated fatty acid (e.g. omega-3), is within the scope of the invention.

In the case of cocoa polyphenol, the improvement is achieved either (i) by adding cocoa polyphenol or a derivative thereof to a food that does not contain cocoa polyphenol or (ii) when the food traditionally contains cocoa polyphenols, such as for example chocolate, by enhancing the polyphenol level over the one found in the traditionally prepared food. The enhancement may be achieved by adding additional cocoa polyphenols, for example, in a form of an extract; by adding cocoa polyphenol in combination with another polyphenol containing ingredient (e.g. nut skins); by manipulating the cocoa ingredients processing and cocoa bean selection, as described above, to preserve cocoa polyphenol in the cocoa ingredient used for the manufacture of the food product; or by manipulating the chocolate manufacturing process as described above. Thus, these foods (including beverages) contain an "elevated level of polyphenols" (including cocoa procyanidins) in comparison to comparative conventional foods (including beverages). An example of a chocolate having an elevated level of polyphenol occurs when a chocolate manufacturer adds a cocoa extract containing cocoa polyphenols to its previously commercially available product. The foods may also be referred to as "high cocoa polyphenol foods," i.e., they contain higher levels of polyphenol than their traditional counterparts.

The foods comprising cocoa polyphenols and at least one cholesterol lowering agent (e.g. a sterol and/or stanol based cholesterol lowering agent), and optionally L-arginine, calcium, potassium, magnesium, vitamin E, vitamin C, any of the vitamins of the B complex, a carotenoid, guar gum, or a mono or polyunsaturated fatty acid (e.g. omega-3) may be adapted for human or veterinary use, and include pet foods. The food may be other than a confectionery, however, the preferred cholesterol lowering food is a confectionery such as a standard of identity (SOI) and non-SOI chocolate, such as milk, sweet and semi-sweet chocolate including dark chocolate, low fat chocolate and a candy which may be a chocolate covered candy. Other examples include a baked product (e.g. brownie, baked snack, cookie, biscuit) a condiment, a granola bar, a toffee chew, a meal replacement bar, a spread, a syrup, a powder beverage mix, a cocoa or a chocolate flavored beverage, a pudding, a rice cake, a rice mix, a savory sauce and the like. If desired, the foods may be chocolate or cocoa flavored. Food products that contain L-arginine, in addition to the cocoa polyphenol and the cholesterol lowering agent, are preferably chocolates and candy bars, such as granola bars, containing nuts, for example, peanuts, walnuts, almonds, and hazelnuts. It should be noted that the addition of nuts with skins to the food described herein may also increase the total polyphenol content since, for example, peanut skins contain about 17% procyanidins and almond skins contain about 30% procyanidins. In one embodiment, the nut skins are added to the nougat of a chocolate candy containing a cholesterol lowering agent.

In preferred embodiments, the non-chocolate food products containing a cholesterol lowering agent contains from about at least 5 μg/g to about 10 mg/g, and, for example, at least 5 μg/g food product, preferably at least 10 μg, more preferably at least 100 μg/g of cocoa procyanidins. If desired, the non-chocolate food products can contain much higher levels of cocoa procyanidins than those found in the chocolate food products described below.

A particularly preferred food product is a cholesterol lowering chocolate confectionery and the most preferred is dark chocolate. In certain embodiments, the chocolate comprises at least 3,600 μg, preferably at least 4,000 μg, preferably at least 4,500 μg, more preferably at least 5,000 μg, and most preferably at least 5,500 μg cocoa procyanidins per gram of chocolate, based on the total amount of nonfat cocoa solids in the product. In other embodiments, the chocolate contains at least 6,000 μg, preferably at least 6,500 μg, more preferably at least 7,000 μg, and most preferably at least 8,000 μg of cocoa procyanidins per gram, and even more preferably 10,000 based on the nonfat cocoa solids in the product.

A cholesterol lowering milk chocolate confectionery may have at least 1,000 μg, preferably at least 1,250 μg, more preferably at least 1,500 μg, and most preferably at least 2,000 μg cocoa procyanidins per gram, based on the total amount of nonfat cocoa solids in the milk chocolate product. In the preferred embodiment, the milk chocolate contains at least 2,500 μg, preferably at least 3,000 μg, more preferably at least 4,000 μg, and most preferably at least 5,000 μg cocoa procyanidins per gram, based on the total amount of nonfat cocoa solids in the milk chocolate product.

The amount of L-arginine in the food products can vary. Typically, cocoa contains between 1 to 1.1 grams of L-arginine per 100 grams of partially defatted cocoa solids. It can range from 0.8 to 1.5 per 100 grams of cocoa. The chocolate food products of this invention contain L-arginine in an amount greater than that which naturally occurs in the cocoa ingredients. Knowing the amount of cocoa ingredients and L-arginine used in the food product, one of ordinary skill in the art can readily determine the total amount of L-arginine in the final product. The food product will generally contain at least 5 μg/g, preferably at least 30 μg/g, or at least 60 μg/g, even more preferably at least 200 μg/g food product.

The amount of the cholesterol lowering agent in the food will depend on the type of the agent used and can be determined by a person of skill in the art based on the guidance in the specification, particularly daily dosages provided below, and the knowledge in the art. A food comporition, for example, may contain from about 0.5 to about 10 g per 45 g serving size, preferably about 1.5 to about 5 g per 45 g serving size, most preferably about 2 to about 4.5 g per 45 g serving size of sterols/stanols. With respect to soy protein and soluble fiber from oats, FDA has provided minimum amounts per food serving to be able to make a health claim. According to the FDA, a food serving containing beta-glucan must contain at least 0.75 g, and the food serving containing soy protein must contain at least 6.25 g soy protein. These values may also be used as a guide for determining the amount of these cholesterol lowering agents in the food.

In one of the preferred embodiments, a daily effective amount of the cholesterol lowering agent and the cocoa polyphenol is provided in a single serving. Thus, a cholesterol lowering confectionery (e.g. chocolate) contains at least 1.5 (e.g. 1.5–4.5 g) per serving sterol/stanol and at least about 100 mg/serving about (e.g. 150–200, 200–400 mg) serving cocoa procyanidins.

Pharmaceuticals containing polyphenols having the properties recited herein (e.g. cocoa polyphenols or derivatives thereof) in combination with a cholesterol lowering agent and optionally L-arginine, may be administered in a variety of ways such as orally, bucally, nasally, rectally, intravenously, parenterally and topically. A person of skill in the art will be able to determine a suitable cholesterol lowering agent depending on the mode of administration. Thus, dosage forms adapted for each type of administration are within the scope of the invention and include solid, liquid and semi-solid dosage forms, such as tablets, capsules, gelatin capsules (gelcaps), bulk or unit dose powders or granules, emulsions, suspensions, pastes, creams, gels, foams or jellies. Sustained-release dosage forms are also within the scope of the invention and may be prepared as described in U.S. Pat. Nos. 5,024,843; 5,091,190; 5,082, 668; 4,612,008 and 4,327,725, relevant portions of which are hereby incorporated herein by reference. Suitable pharmaceutically acceptable carriers, diluents, or excipients are generally known in the art and can be determined readily by a person skilled in the art. The tablet, for example, may comprise an effective amount of the cocoa polyphenol-containing composition and optionally a carrier, such as sorbitol, lactose, cellulose, or dicalcium phosphate. The dietary supplement containing cocoa polyphenols, at least one cholesterol lowering agent, and optionally L-arginine, may be prepared using methods known in the art and may comprise, for example, nutrient such as dicalcium phosphate, magnesium stearate, calcium nitrate, vitamins, and minerals.

Further within the scope of the invention is a package comprising a food, a dietary supplement or a pharmaceutical, and a label indicating (i) the presence of, or an enhanced content of polyphenols and/or derivatives thereof and (ii) the presence of a cholesterol lowering agent. Optionally, the label may indicate the L-arginine content, the beneficial properties of the combined polyphenol(s), cholesterol lowering agent(s) and optionally L-arginine and instructions for use. As used herein, the beneficial properties include lowering plasma cholesterol, total and LDL, inhibiting COX activity (including COX 1 activity), inhibiting LOX activity, enhancing nitric oxide production, increasing the ratio of atherostatic to atherogenic factors (i.e., eicosanoid and endothelins produced) and inhibiting oxidation of LDL, which in turn, individually or in combination, help reduce vasoconstriction and platelet aggregation, inhibit monocyte adhesion, inhibit excessive proliferation of vascular smooth muscle, reduce thrombosis, reduce blood pressure, and thus reduce risks associated with vascular and cardiovascular diseases such as atherosclerosis and cardiovascular disease.

Also within the scope of the invention is a package comprising (i) a composition comprising a polyphenol having at least one of the following properties: inducing vasorelaxation, inhibiting COX activity, inhibiting LOX activity, inhibiting oxidation of LDL, enhancing NOS activity, increasing the level of NO, inhibiting platelet aggregation, monocyte adhesion and proliferation of vascular smooth muscle, reducing blood pressure, reducing thrombosis, and modulating oxidative stress, and a cholesterol reducing agent, for example, a sterol and/or stanol based cholesterol reducing agent; and (ii) a label and/or instructions for use of the composition to promote vascular health (the term cardiovascular health may also be used) and/or reduce the risk of heart disease. When a sterol and/or stanol based cholesterol reducing agent is used the label and/or instructions may recite that the composition promotes or enhances absorption of the polyphenol. The label and/or instructions may also indicate other beneficial properties mentioned above. These are lowering plasma cholesterol, total and LDL, inhibiting COX activity, inhibiting LOX activity, enhancing nitric oxide production, increasing the ratio of atherostatic to atherogenic factors (i.e., eicosanoid and endothelins produced) and inhibiting oxidation of LDL, which in turn, individually or in combination, help reduce vasoconstriction and platelet aggregation, inhibit monocyte adhesion, inhibit excessive proliferation of vascular smooth muscle, reduce thrombosis, reduce blood pressure, and thus reduce risks associated with vascular and cardiovascular diseases such as atherosclerosis and cardiovascular disease.

Also within the scope of the invention are methods for treating and/or preventing diseases and/or conditions associated with, or modulated by, COX activity, LOX activity, NO production, NOS activity, oxidation of LDL and increased plasma total and LDL cholesterol. As used herein, "treatment" means improving an existing medical condition, for example, high blood pressure or atherosclerosis, by affecting the pathology of the disease or the symptoms associated therewith. The term "preventing" means reducing the risks associated with developing a disease, including reducing the onset of the disease. The prevention or prophylaxis may be used in an individual known to be at high risk of developing a disease or in a population at large for maintaining good health, for example, maintaining vascular health. The methods may be used in a human or a veterinary animal, such as a dog, a cat, and a horse.

Diseases and/or conditions associated with, or modulated by, COX activity, LOX activity, NO production, NOS activity, oxidation of LDL and/or high cholesterol include atherosclerosis, hypertension, coronary heart disease (CHD), cerebrovascular disease, heart attack, stroke, peripheral vascular disease and kidney failure. Also included are methods for treating or preventing hypercholesterolemia (including mild hypercholesterolemia), inducing vasorelaxation, inhibiting COX (including COX1) and LOX activity inhibiting oxidation of LDL, enhancing NOS activity and increasing the level of NO, inhibiting platelet aggregation, monocyte adhesion and proliferation of vascular smooth muscle, reducing blood pressure, reducing thrombosis, and modulating oxidative stress.

The methods comprise administering to a mammal, preferably a human or a veterinary animal, an amount of the composition comprising a polyphenol, for example, a cocoa polyphenol and a cholesterol reducing agent, and optionally L-arginine, effective to treat, prevent or achieve at least one of the above beneficial effects in addition to cholesterol lowering. The methods may further comprise determining the effectiveness of the treatment by, for example, determining plasma cholesterol levels.

The composition may be administered to a healthy mammal for prophylactic purposes or to a mammal in need of a treatment or having at least one of the risk factors associated. Any individual having at least one of the risk factors associated with vascular health problems is a subject for administration of the compositions described herein. The individuals with a familial history of elevated cholesterol levels, peri- or post-menopausal females, postmenoposal females w/myocardial post-ischaemic damage, surgically or chemically induced estrogen deficient females, the aged, those with hyperglycemia, diabetes, hypertension, and obesity, and cigarette smokers are all susceptible individuals in need of the treatment described herein. Other populations of mammals that are susceptible to developing vascular health problems will be apparent to one skilled in the art.

The methods are particularly useful for treatment or prevention of restenosis. Each year about 330,000 patients in the United States undergo coronary and/or peripheral angioplasty (Marx, 265 Science 320, 1994), a procedure designed to open up blood vessels, e.g., coronary arteries, clogged by atherosclerotic plaques to restore normal blood flow. Nearly 33% of these patients, however, develop restenosis, i.e., the treated arteries become quickly clogged again. These patients are no better off, and sometimes worse off, than they were before angioplasty. Excessive proliferation of smooth muscle cells (SMCs) in blood vessel walls contributes to restenosis. Thus, the compositions containing cocoa polyphenol and a cholesterol lowering agent (and optionally L-arginine) may be administered prior to angioplasty, or soon thereafter as determined by the skilled medical practitioner.

Veterinary animal, for example dogs, cats and horses, may be administered the above described compositions to treat or prevent heart failure, valvular degeneration and chronic renal failure. For example, compositions of the invention may be administered to dogs to address the following conditions: chronic valvular disease (endocardiosis or myxomatous degeneration of the atrioventricular valves), dilated cariomyopathy, pericarial disease, endocarditis, primary arrhythmias and heartworm disease.

A method of enhancing absorption of a polyphenol into the blood of a human or a veterinary animal (e.g. a pet) is also provided. The method, which in essence enhances the bioavalability of polyphenols that are beneficial for the human or animal health, comprises administering to the human or a veterinary animal, in combination, a (i) polyphenol having at least one of the following properties: inducing vasorelaxation, inhibiting COX activity, inhibiting LOX activity, inhibiting oxidation of LDL, enhancing NOS activity, increasing the level of NO, inhibiting platelet aggregation, monocyte adhesion and proliferation of vascular smooth muscle, reducing blood pressure, reducing thrombosis, and modulating oxidative stress, and (ii) a sterol and/or stanol based cholesterol reducing agent. The polyphenol may be, for example, a flavanol or a flavonol, the examples of which were provided above. The method may be practiced by administering the polyphenol and the sterol/stanol as components of the same composition or separately.

The effective amount may be determined by a person skilled in the art using the guidance provided herein and the general knowledge in the art. For example, to obtain the cholesterol lowering effects using sterols/stanols, more than what is normally found in the average diet of a non-vegetarian should be administered. A person on a typical North American diet consumes about 200–400 mg/day. Thus, when phytosterol, such as sitosterol, is used to reduce cholesterol levels, about at least 1 g/day, preferably at least about 3 g/day should be administered. Preferably, from at least about 1 g/day, preferably at least about 4.5 g/d, to about 20 g/day is used. However, the amount will vary depending on the cholesterol lowering potency of the phytosterol so that, for example, if a more potent sitostanol is used, the effective amount may be as low as about one to about three g/day. The amounts may be determined using the analytical procedure described in Roger et al., J. Amer. Oil Chem. Soc. 70(30) 1993 and Carpenter, et al., J. Amer. Oil Chem. Soc. 71(8) 1994. Soy protein may be administered, for example, at least about 25 g/day. Further guidance can be found in Recommended Daily Allowances, $9^{th}$ ed., National Res. Council/National Acad. Sci., Washington, D.C. Soluble fiber may be administered for example at at least 3 g/day. Cocoa polyphenol may be administered at from about 50 mg/day to about 1000 mg/day, preferably from about 100–150 mg/day to about 900 mg/day, and most preferably from about 300 mg/day to about 500 mg/day. However, given that polyphenols naturally occur in foods and are non-toxic, amounts higher than stated above may be used. L-arginine may be administered from about 2 g/day to about 50 g/day, preferably from about 3 g/day to about 10 g/day, and most preferably from about 6 g/day to about 8 g/day. Here as well, given that L-arginine naturally occurs in foods, amounts higher than stated above may be used. Polyphenols generally may be administered in the amounts known in the art. The enhanced absorption in the presence of sterols/stanols may also be taken into consideration when determining the effective amount.

The treatments/preventive administration may be continued as a regimen, e.g., daily, monthly, bimonthly, biannually, annually, or in some other regimen, as determined by the skilled medical practitioner for such time as is necessary. Preferably, the composition is administered daily, most preferably two or three times a day, for example, morning and evening to maintain the levels of the effective compounds in the body of the mammal. To obtain the most beneficial results, the composition may be administered for at least about 30 to about 60 days. These regiments may be repeated periodically.

The invention is further described in the following non-limiting examples.

EXAMPLES

Example 1

The Effect of Cocoa Procyanidins on Lipoxygenase Activity

The phenol fractions (monomer to hexamer) and extracts (crude acetone and pentamer enriched) were prepared as described in Examples 1–5 of U.S. Pat. No. 5,554,645 to Romanczyk et al. and Example 5 of International Appl. No. PCT/US97/05693 published as WO97/36497. Lipoxygenase Type I-B from soybean, linoleic acid (approx. 99%), Tween 20 (Polyoxyethylene-sorbitan monolaurate), and control phenols (Nordihydroguaiaretic acid (NDGA), (+)-catechin and (−)-epicatechin) were obtained from Sigma Chemical.

Linoleic acid was solubilized using the emulsifier Tween 20 according to Grossman & Zakut (Methods Biochem. Anal. 25:303–329, 1979). Lipoxygenase was dissolved in PBS pH 8.6 at 5000 U/mL. Cocoa phenols were dissolved in pure water and diluted from the following stock solutions. 1 to 6mer were dissolved at 1 mM, extracts at 1 mg/mL (1 g crude acetone extract/L~3.0 mM monomer, 1 g 5mer enriched extract/L~3.4 mM).

Inhibition was calculated for each sample set of 6 reaction cuvettes (1 control with water, 5 experimental with phenol in water) according to the formula: % inhibition=(Δ abs. control−Δ abs. experimental)/Δ abs. control)×100. The reaction mixtures contained dissolved linoleic acid (100 $\mu$M) in PBS pH 7.4 plus/minus test phenols in water. The reaction was initiated by adding lipoxygenase for a final concentration of 100 U/mL. Conjugated diene measurement of hydroperoxide formation of linoleic acid was measured by recording kinetic scans over 5 or 10 minutes on a Beckman DU-600 UV spectrophotometer (at 37° C., absorbance 234 nm).

The high UV absorbance of the cocoa components did not allow the measurement of $IC_{50}$ at actual concentrations. For this reason an $IC_{50}$ value was calculated by extrapolating the logarithmic regression curve (% inhibition over log phenol concentration) to the concentration at which 50% inhibition of lipoxygenase activity was achieved by the test substance. Extrapolated $IC_{50}$ values give a rough approximation of the lipoxygenase inhibitory activity of cocoa polyphenol extracts.

NDGA is an established inhibitor of soybean and several mammalian lipoxygenases (Kemal et al, Biochemistry 26:7064–7072, 1987). It is commercially used as an antioxidant in fats and oils. NDGA serves as a positive control since the $IC_{50}$ value of $2 \times 10^{-6}$ M was not reached by other test phenols. (+)-catechin and (−) epicatechin are assumed to be structurally similar to the cocoa polyphenol monomer.

Phenols were compared on a molar basis. Lipoxygenase inhibition by (+)-catechin ($3 \times 10^{-3}$M) was two magnitudes stronger than by (−)-epicatechin ($3 \times 10^{-1}$ M) and very similar to inhibition by +cocoa monomer ($5 \times 10^{-3}$M), dimer ($2 \times 10^{-3}$M) and trimer ($2 \times 10^{-3}$M). Lipoxygenase inhibition by the higher oligomers correlated less well with the log of the molar concentration. At final concentrations of 0.3 to 25 $\mu$M, the tetramer, pentamer and hexamer inhibited 5–30% lipoxygenase activity. However, phenol concentration and inhibition did not correlate significantly. The crude acetone extract exhibited a concentration dependent lipoxygenase inhibition ($IC_{50}$=5 $\mu$M, compared on a monomer basis) approximately 3 magnitudes weaker than monomer to trimer fractions. The pentamer enriched extract ($IC_{50}$=59M) did not inhibit lipoxygenase activity at a meaningful level.

The soybean lipoxygenase inhibitory activity of cocoa phenol extracts resemble that of (+)-catechin. There is little difference among the activities of the monomer to trimer if compared on a molar basis, suggesting a steric inhibition of the enzyme. The inhibition may be specific for the low molecular weight components (monomer to trimer) since the tetramer to hexamer compounds show considerably less lipoxygenase inhibitory activity and the pentamer enriched extract is less inhibiting than the crude extract, which contains more of the monomer to trimer oligomeric fractions. Thus, cocoa polyphenols inhibit soybean lipoxygenase either by chelating the prosthetic iron ion, or by scavenging free radicals via phenolic hydroxyl groups in the oxidation reaction, which includes free radical intermediates. Larger oligomers (the tetramers to hexamers) may be sterically hindered and thus may not be capable of reading the catalytic site of the enzyme.

Example 2

The Effects of Cocoa Procyanidin Extracts and Cocoa Procyanidin Oligomeric Fractions on Basal Endothelial Cell Release of Prostanoids and Total Endothelin (ET)

The effect of purified procyanidin monomers and pentamers from cocoa polyphenol extract on the release of the prostanoids prostacyclin, prostaglandin (PGE2) and thromboxane, and total endothelin on bovine and human endothelial cells in culture was studied.

Indomethacin was purchased from Cayman (Ann Arbor, Mich. USA). Monomeric and pentameric procyanidin fractions were purified from procyanidin-enriched cocoa beans (processed according to the methods described in U.S. Pat. No. 6,015,913, issued Jan. 18th, 2000), by the methods described in Examples 1–5 of U.S. Pat. No. 5,554,645, issued Sep. 10th, 1996.

The samples were analyzed by the method of Hammerstone et al., (J. Agric. Food Chem., 47:2:490–496, 1999). Confirmation of molecular weight purity was obtained by mass spectrometry.

Bovine aortic endothelial cells (BAEC) and human aortic endothelial cells (HAEC) were cultured in Eagle's minimum essential medium (EMEM) as described previously by Schramm et al., (J. Nutr. Biochem. 8:647–651, 1997; J.Agric. and Food. Chem. 46(5): 1900–1905, 1998).

ECs (passage <11) were seeded onto 24-well plates with EMEM containing 2 mmol glutamine/L, 10% fetal bovine serum, 100 units penicillin/L, 0.1 mg streptomycin/L, and 0.25 pg amphotericin/L. Confluent cells were treated in 250 ml of phenol red-free EMEM containing treatment compounds where applicable. Medium incubated with EC's was analyzed after application of procyanidin fractions (10, 20, and 30 pmol/L) and incubation with ECs for 0 and 20 min. The medium was stored at −70° C. until analyzed by immunoassay as described below. EC integrity was monitored by Trypan Blue exclusion as described in Bioadjieras et al., Methods in Lab. Invest. 50:239–246, 1984.

Immunoassay procedures were conducted as described by Westcott et al, Prostaglandins 32:857–873, 1986; Yakota et al, Adv. Prostgl.Thrombox. Leukot. Res. 15:33–34, 1985; Schramm et al, 1997; 1998;1999. Medium total ET (ET-1+ ET-2+ET-3) was measured with Cayman immunoassay #583151. The prostacyclin ($PGI_2$) metabolite 6-keto prostaglandin F1-alpha was measured with Cayman enzyme immunoassay #515211, the thromboxane ($TXA_2$) metabolite $TXB_2$ was measured with Cayman enzyme immunoassay 519031, and $PGE_2$ was determined with Cayman immunoassay #514016.

The established assay conditions mimic those used previously to show that a wine fraction with mass <3000 da. induced different effects on EC prostanoid synthesis than did a wine fraction having a mass of >3000 (Schramm et al, J.Agric. and Food. Chem. 46(5): 1900–1905, 1998). The effects on basal cell function were examined. Neither cell viability nor cell morphology was effected by cocoa procyanidin treatments. Each milliliter of control medium incubated with BAECs for 20 min contained 73.5=+/−0.044 ng TXB2 and 294+/−6.3 pg PGE2.

As shown in FIG. 2, the addition of the monomeric or pentameric cocoa procyanidins to medium incubated with BAECs for 20 min altered medium prostanoid and ET concentrations when compared to the control medium alone. Media containing either monomeric ($A^1$) or pentameric ($A^2$) procyanidins contained more 6-keto-$PGF^1$-alpha than the control medium. Medium $PGE^2$ was reduced by the monomeric fraction (B1) in a dose-dependent manner and by the pentameric fraction ($B^2$) at 30 μM. No significant effect of either cocoa procyanidin fraction was noted on medium TXB (C1–2). Although the monomeric and pentameric cocoa procyanidin fractions had similar effects on medium 6-keto-$PGF^1$-alpha and $PGE^2$, they had opposite effects on medium ET, with the monomeric fraction ($D^1$) increasing the concentration of ET in the culture medium at 30 μM and the pentameric fraction ($D^2$) decreasing medium ET concentration in a dose dependent manner.

Figure 3A:
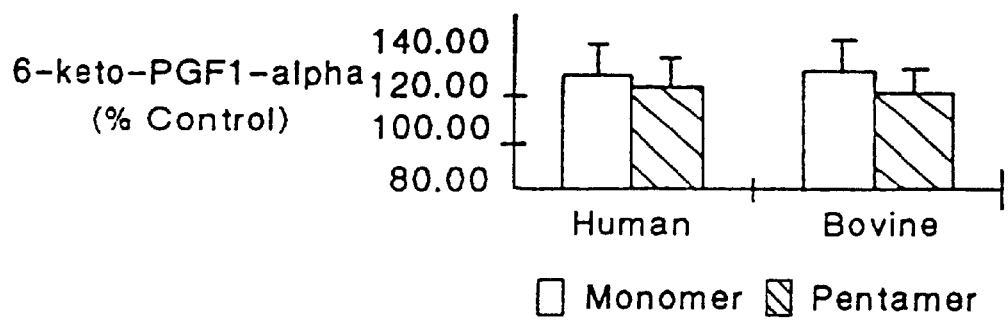
FIGS. 3A–B show the effects of cell species on procyanidin induced alterations in EC release of prostacyclin and endothelin.
Figure 3B:
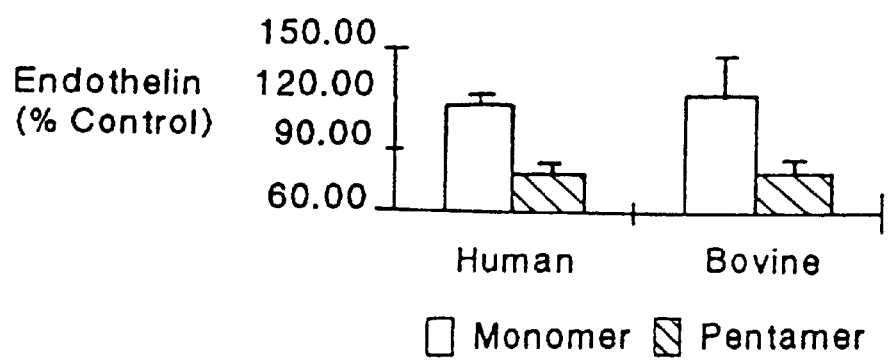

Data in FIGS. 3A–B demonstrate the similar manner in which monomeric and pentameric cocoa procyanidins affected aortic ECs from cows (BAEC) and humans (HAEC).

The above data demonstrate that the cocoa procyanidins induce eicosanoid and endothelin effects which relax vessels relaxation and decrease platelet aggregation/thrombus formation, i.e., induction of prostacyclin and inhibition of endothelin and prostaglandin.

Example 3

The Effects of the Consumption of a Procyanidin-enriched Cocoa Beverage on Platelet Activity The effects of consumption of a cocoa beverage on modulation of platelet activation and primary haemostasis were studied.

Thirty healthy, non-smoking adults with no history of heart disease or haemostatic disorders were divided into 3 treatment groups: (a) 10 subjects (4 males and 6 females, 24–49 years of age) who consumed a cocoa beverage (b) 10 subjects (4 males and 5 females, 26–50 years of age) who consumed a caffeine beverage as a control, and (c) 10 subjects (4 males, 6 females, 24–50 years of age) who consumed water as a control. All women were premenopausal and were not taking estrogens. Participants were instructed to abstain from nonsteroidal, anti-inflammatory medication for at least 4 days, from alcoholic beverages for at least 2 days, and from caffeine- or theobromine-containing foods for at least 24 hours before the test and during the test day.

Blood was obtained from each subject between 8 and 10 AM. Samples were collected in two 5-ml evacuated tubes containing 0.5 ml of 3.2% buffered sodium citrate solution (Becton Dickinson, Franklin Lakes, N.J.). Test subjects then drank 300 ml of a beverage containing 18.75 g of procyanidin enriched cocoa powder (which provided approximately 960 mg of total procyanidins, 17 mg caffeine and 285 mg theobromine) and 12.5 g of sucrose mixed with distilled water (see Adamson, G. E. et al., J. Ag. Food Chem.; 1999; 47 (10) 4184–4188). Control subjects drank either a beverage containing 17 mg caffeine and 12.5 g sucrose or plain water. Additional blood samples were obtained 2 and 6 hours after consumption of the beverages. One female subject was not present for the 6-hour blood draw after cocoa consumption.

Procyanidins were quantified as follows: a composite standard was made using commercially available (−)-epicatechin, and dimers through decamers obtained in a purified state by the methods described in Hammerstone, J. F. et al., J. Ag. Food Chem.; 1999; 47 (10) 490–496, Lazarus, S. A. et al., J. Ag. Food Chem.; 1999; 47 (9); 3693–3701 and Adamson, G. E. et al., J. Ag. Food Chem.; 1999; 47 (10) 4184–4188. Standard Stock solutions using these compounds were analyzed using the normal-phase HPLC method described in the previously cited Adamson reference, with fluorescence detection at excitation and emission wavelengths of 276 nm and 316 nm, respectively. Peaks were grouped and their areas summed to include contributions from all isomers within any one class of oligomers and calibration curves were generated using a quadratic fit. Monomers and smaller oligomers had almost linear plots which is consistent with prior usage of linear regression to generate monomer-based and dimer-based calibration curves.

These calibration curves were then used to calculate procyanidin levels in samples prepared as follows: First, the cocoa or chocolate sample (about 8 grams) was defatted using three hexane extractions (45 mL each). Next, one gram of defatted material was extracted with 5 mL of the acetone/water/acetic acid mixture (70:29.5:0.5 v/v). The quantity of procyanidins in the defatted material was then determined by comparing the HPLC data from the samples with the calibration curves obtained as described above (which used the purified oligomers). The percentage of fat for the samples (using a one gram sample size for chocolate or one-half gram sample size for liquors) was determined using a standardized method by the Association of Official Analytical Chemists (AOAC Official Method 920.177). The quantity of total procyanidin levels in the original sample (with fat) was then calculated. Calibration was performed prior to each sample run to protect against column-to-column variations.

Within 10 minutes of collection of blood samples, whole blood was incubated in polystyrene tubes for 5 minutes at room temperature with 10 μl HEPES buffer (pH 7.4, unstimulated control), 20 or 100 μM ADP or 20 μM epinephrine (BioData, Horsham, Pa.) in the presence or absence of the peptide Arg-Gly-Asp-Ser (Sigma, St. Louis, Mo.). After 5 minutes, samples were suspended in 1 ml HEPES buffer and 100 μl of sample were transferred to tubes containing saturating concentrations (20 μL) each of the following fluorescent-labeled monoclonal antibodies: PAC 1-fluorescein isothiocyanate (FITC), anti-CD62P-phycoerythrin (PE) and anti-CD42a-PerCP. PAC1 recognizes the activated conformation of the fibrinogen-binding receptor GPIIb-IIIa and anti-CD62P recognizes P-selectin, present on the surface of activated platelets. Anti-CD42a recognizes GPIb-IX, which is on the surface of both activated and resting platelets. Mouse IgG, FITC and mouse IgG, PE were used as isotype controls. The Arg-Gly-Asp-Ser-peptide was used to block binding of the PAC1 antibody to platelets and thus set the negative control marker on the flow cytometer. Antibodies and isotype controls were purchased from Becton Dickinson Immunocytometry Systems, Inc., San Jose, Calif.

Whole blood samples, in the presence and absence of the agonists ADP and epinephrine, were incubated with monoclonal antibodies or isotype control for 20 minutes in the dark at room temperature. Samples were then fixed in filtered 1% paraformaldehyde (pH 7.2) and stored in the dark at 2–8° C. All samples were analyzed within 48 hours on a FACScan flow cytometer using LYSYS II software. The flow cytometer performance was verified using 1, 2 and 10 $\mu$m calibration beads (Becton Dickinson Immunocytometry Systems, Inc., San Jose, Calif. and Flow Cytometry Systems, Research Triangle Park, N.C.). Twenty-thousand events were collected in list mode with all light-scatter and fluorescence parameters in logarithmic mode. Platelets were gated on the basis of lightscatter and CD42a expression. Activated platelets were defined as the percentage of CD42a positive events coexpressing the activated conformation of GPIIb-IIIa or P-selectin. Platelet microparticles were defined as the percentage of CD42a positive events less than 2 $\mu$m in size.

One blood sample drawn at each of the three study time points was analyzed within four hours using a platelet function analyzer (PFA-100™, Dade Behring International, Miami, Fla.) according to the manufacturer's directions. See Mammen et al, Sem. Thromb. Hemostas. 24:195–202, 1998, and Fressinaud et al, Blood 91:1325–31, 1998. Function was measured as a closure time in seconds, which is defined as the time required for blood to occlude an aperture in the test cartridge membrane.

Data from each treatment or control group were analyzed for differences using Friedman's repeated measures ANOVA on ranks (SigmaStat for Windows, SPSS, Richmond, Calif.). Student-Newman-Keuls multiple comparison method was used to identify differences between baseline and 2 and 6 hours post-consumption results. P values less than 0.05 were considered statistically significant.

Cocoa consumption suppressed unstimulated (P=0.035, FIG. 4A) and ex vivo epinephrine-induced (P=0.008, FIG. 4B) activated GPIIb-IIIa expression at 2 and 6 hours after ingestion. The median percentages of platelets expressing activated GPIIb-IIIa without stimulation were 0.9, 0.5 and 0.3% and in response to epinephrine were 9.6, 6.8 and 3.3% at times zero, 2 and 6 hours, respectively, post consumption. In contrast, there was an increase in epinephrine-stimulated activated GPIIb-IIIa expression in the control group that drank the caffeine beverage (P=0.048, median=5.3, 6.5 and 7.5% at times zero, 2 and 6 hours post consumption). There was no change in the control group that drank water.

The cocoa decreased 20 $\mu$M ADP-induced activated GPIIb-IIIa expression on platelets 2 and 6 hours after consumption (P<0.001, FIG. 4C, median=58.5, 44.2 and 38.8% at times zero, 2 and 6 hours post consumption, respectively). The trend suggested decreased activated GPIIb-IIIa expression on platelets after cocoa consumption when activation was induced by 100 pm ADP (P=0.067, median=76.5, 68.7 and 57.6% at times zero, 2 and 6 hours post consumption, respectively). There was no change in ADP-induced activated GPIIb-IIIa expression in groups consuming the caffeine beverage and water controls.

A non-significant trend toward decreased P-selectin expression was observed after cocoa consumption (P=0.053, FIG. 5A). Cocoa consumption decreased 20 $\mu$M ADP-induced P-selectin expression 2 and 6 hours after consumption (P=0.007, FIG. 5C) and 100 $\mu$M ADP-induced P-selectin were 56.1, 54.7 and 41.7% at time zero, 2 and 6 hours post consumption, respectively.

There was no evidence of platelet stimulation or inhibition in the control groups that consumed the caffeine-containing beverage or water.

The number of platelet microparticles detected by flow cytometry after consumption of the cocoa beverage was decreased from baseline at 2 hours and was further decreased at 6 hours (see Table 1). In contrast, the number of platelet microparticles was increased at 2 and 6 hours after consumption of water and at 6 hours after consumption of the caffeine-containing beverage. Platelet microparticles are haemostatically active, phospholipid rich microvesicles that are formed during physiologic platelet activation.

TABLE 1

MICROPARTICLE FORMATION AFTER CONSUMPTION OF A COCOA BEVERAGE.[†]

| TIME | WATER | CAFFEINE BEVERAGE | COCOA BEVERAGE |
|---|---|---|---|
| BEFORE CONSUMPTION | 0.7 (0.3–1.2) | 1.0(0.6–1.8) | 1.9(1.0–5.0) |
| 2 H POST CONSUMPTION | 1.2 (0.7–1.6)* | 1.1(0.6–2.0) | 1.0(0.7–1.4)* |
| 6 H POST CONSUMPTION | 1.3 (0.8–2.1)* | 1.5(1.2–2.3) | 0.6(0.4–1.1)* |

[†]Percentage microparticles of total CD42 positive events. Values denote median (range), n = 10 per group.
*Significantly different from "Before Consumption" (P < 0.05).

Six hours following consumption of the cocoa beverage, collagen-epinephrine-induced closure time was prolonged (see Table 2). This indicates delayed platelet-related primary haemostasis with cocoa consumption. A trend toward prolonged closure time was observed after collagen-ADP-induction (p=0.097); closure time was not changed in the caffeine control group.

TABLE 2

PLATELET FUNCTION ANALYSIS.[†]

| TIME | COLLAGEN-EPINEPHRINE COCOA BEVERAGE | COLLAGEN-EPINEPHRINE CAFFEINE BEVERAGE | COLLAGEN-ADP COCOA BEVERAGE | COLLAGEN-ADP CAFFEINE BEVERAGE |
|---|---|---|---|---|
| BEFORE CONSUMPTION | 125 (61–80) | 104 (61–180) | 83 (60–133) | 77 (52–95) |

TABLE 2-continued

PLATELET FUNCTION ANALYSIS.[†]

| TIME | COLLAGEN-EPINEPHRINE COCOA BEVERAGE | COLLAGEN-EPINEPHRINE CAFFEINE BEVERAGE | COLLAGEN-ADP COCOA BEVERAGE | COLLAGEN-ADP CAFFEINE BEVERAGE |
|---|---|---|---|---|
| 2 H POST CONSUMPTION | 135 (82–194) | 113 (81–141) | 96 (65–132) | 78 (58–99) |
| 6 H POST CONSUMPTION | 164 (101–262)I* | 114 (79–143) | 94 (66–116) | 82 (67–114) |

[†]Primary platelet-related hemostasis closure time in seconds. Values denote median (range), n = 10 per group.
*Significantly different from "Before Consumption" ($P < 0.05$).
Friedman's Repeated Measure ANOVA on ranks, followed by Student-Newman-Keuls multiple comparison method.

The results showed that consumption of the chocolate beverage modified platelet function in humans. First, platelet activation measured by platelet activation marker expression in response to weak agonists in vitro was decreased following cocoa consumption. Second, platelet microparticle formation was decreased following cocoa consumption. And third, the cocoa consumption caused an aspirin-like effect on platelet function as measured by platelet-related primary haemostasis. The fact that the caffeine beverage control caused an increase in epinephrine-induced activated GPIIb-IIIa expression and microparticle formation would imply that the cocoa procyanidins present in the cocoa beverage are responsible for the inhibition of platelet activation and function.

Example 4

The Effects of the Oral Consumption of Cocoa on the Inhibition of Vascular Endothelium Dependent Relaxation (EDR) by Cholesterol It has been shown that some plant extracts containing flavonoids induce EDR in vitro in rabbit aortas. We studied the effects of chronic oral administration of cocoa on EDR and its protective activity against the loss of EDR that occurs with cholesterol feeding. New Zealand White rabbits were fed 4 diets for 7 weeks: (1) chow, (2) chow+200 mg cocoalday, (3) 2% cholesterol for 3 weeks followed by 4 weeks of chow, (4) 2% cholesterol for 3 weeks followed by 4 weeks of chow+200 mg cocoa/day. EDR was measured on aortic rings suspended in organ baths (20 ml). The rings were pre-contracted with norepinephrine (NE) ($10^{-5}$M). EDR to acetylcholine (Ach) and cocoa pentamer extract ($10^{-7}$–$10^{-5}$M) was measured as % relaxation to NE.

| Diet | Serum Cholesterol (3 wks) | EDR to Ach (%) | EDR to Pentamer extract (%) |
|---|---|---|---|
| 1(n = 6) | 52 ± mg/dL | 49.0 ± 5.1 | 46.5 ± 4.5 |
| 2(n = 5) | 30 ± 4 mg/dL | 44.4 ± 5.1 | 44.5 ± 3.6 |
| 3(n = 9) | 1377 ± 218 mg/dL | 16.1 ± 5.0(n = 6)* | 25.5 ± 9.7(n = 3) |
| 4(n = 5) | 1084 ± 266 mg/dL | 42.4 ± 11.3 | 49.5 ± 5.7 |

*significantly different others in the column

Example 5

The Effect of Oral Consumption of Cocoa Procyanidins, Phytosterols and the Combination Thereof The results of this experiment show the effects of feeding a combination of non-esterified phytosterols and phytostanols available from tall oil ("phytosterol") and cocoa powder (CPd), containing about 70 mg/g of total cocoa porcyanidins, on (1) indices of oxidative stress and damage, and (2) on cholesterol levels, as well as the synergistic effect of the combined administration of phytosterols and cocoa procyanidins.

A purified egg shell diet was supplemented with phytosterols (2 wt %) and/or CPd (0, 0.5, 1, 2 wt %) and used to feed male rats for a period of 2 weeks. The rats were divided in eight groups (three rats per group) and fed 20–25 g/day of the control and test diets according to the following:

| Diet + 2% phytosterol (440 mg/d) | | Diet-phytosterol | |
|---|---|---|---|
| Group 1 | 0% CPd(0.0 mg/d) | Group 5 | 0% CPd(0.0 mg/d) |
| Group 2 | .5% CPd(110 mg/d) | Group 6 | .5% CPd(110 mg/d) |
| Group 3 | 1% CPd(220 mg/d) | Group 7 | 1% CPd(220 mg/d) |
| Group 4 | 2% CPd(440 mg/d) | Group 8 | 2% CPd(440 mg/d) |

Water was fed ad lib and consumption was determined by weighing leftover/spilled food collected underneath the food cups. The food intake was measured daily and the rat weight every other day.

The oxidative damage/stress parameters, cholesterol levels and the epicatechin absorption into the blood plasma were measured.

Plasma TBARS were measured using a modification of the method described by Yagi (Biochem Med 15:212–6. 1976). One hundred $\mu$L of whole blood was added to one ml of physiological saline and centrifuged at 1700 g for 15 minutes. The supernatant was collected and frozen at −70° C. until analyzed. Lipids were isolated by precipitating them with a phosphotungstic acid/sulfuric acid system. The lipid fraction was then reacted with thiobarbituric acid, and the resulting adducts measured fluorimetrically, using 1,1',3,3'-tetraethoxypropane as the standard. Results were expressed as nanomoles of MDA per milliliter plasma and as a function of the concentration of plasma polyunsaturated fatty acids.

The 8-Hydroxy-2'-deoxyguanosine (8OH2'dG) was measured as follows. Nuclear DNA was isolated using the Wako DNA Extractor WB kit (Wako Chemical USA, Inc., Richmond, Va.). Tissue (100–250 mg) or cells ($10^6$ cells) were homogenized in the kit lysis buffer and centrifuged at 10,000 g for 20 seconds at 4° C. The pellet was treated with the lysis buffer and the resulting pellet dissolved in the kit enzyme reaction solution. RNase was added to a final concentration of 20 $\mu$g/ml and the sample was incubated at 50° C. for 10 minutes. The kit proteinase solution was added and the 50° C. incubation was continued for an additional hour. The sample was centrifuged at 10,000 g for five minutes at room temperature and the supernatant was treated with the kit NaI solution and isopropanol to purify the DNA. The precipitate was collected at 10,000 g for 10 minutes at room temperature and washed with the kit solutions A and B. The final pellet was briefly air-dried and resuspended in 200 μl of 0.1 mM desferyl/20 mM Na acetate, pH 4.8. The DNA digestion and analysis was carried out according to the method of Shigenaga et al. (Methods Enzymol 234:16–33, 1994) with some modification. Briefly, DNA was digested to nucleotide 5'-monophosphates by incubation with Nuclease P1 at a final concentration of 0.1 mg/ml for 15 minutes at 65° C. The pH was adjusted with 1 M Tris-HCl, pH 8.5, and calf intestine alkaline phosphatase was used to further digest the sample to nucleotides (one hour, 37° C.). The pH of the sample was adjusted with 3 M sodium acetate buffer, pH 5.1, and 0.1 mM EDTA/0.1 mM desferyl was added to prevent metal-mediated oxidation. The sample was put through a 30,000 MW cutoff spin filter and placed in an HPLC injection vial. Samples was analyzed within 48 hours of preparation to prevent artifact formation. For analysis, samples were injected onto a Hewlett Packard 1100 HPLC equipped with an electrochemical detector (ESA, Coulochem II). Separation was achieved using a Supelcosil LC-18-DB column (150×4.6 mm, 3 micron particle size) and mobile phase of 100 mM Na acetate buffer, pH 5.2, with 5% methanol, isocratic, at a flow rate of 1.0 ml/min. OH$^8$dG was detected at 450 mV using electrochemical detection and 2'-deoxyguanosine (dG) was detected at 248 nm using UV detection. Levels of OH$^8$dG were expressed relative to the amount of dG in the samples.

Epicatechin absorption was measured as described in Rein et al., J. of Nutr., 2000, 130 (8S), 2109S–2114S.

Results

The results establish unexpected benefits of the combined administration of phytosterols and polyphenols.

Figure 6:
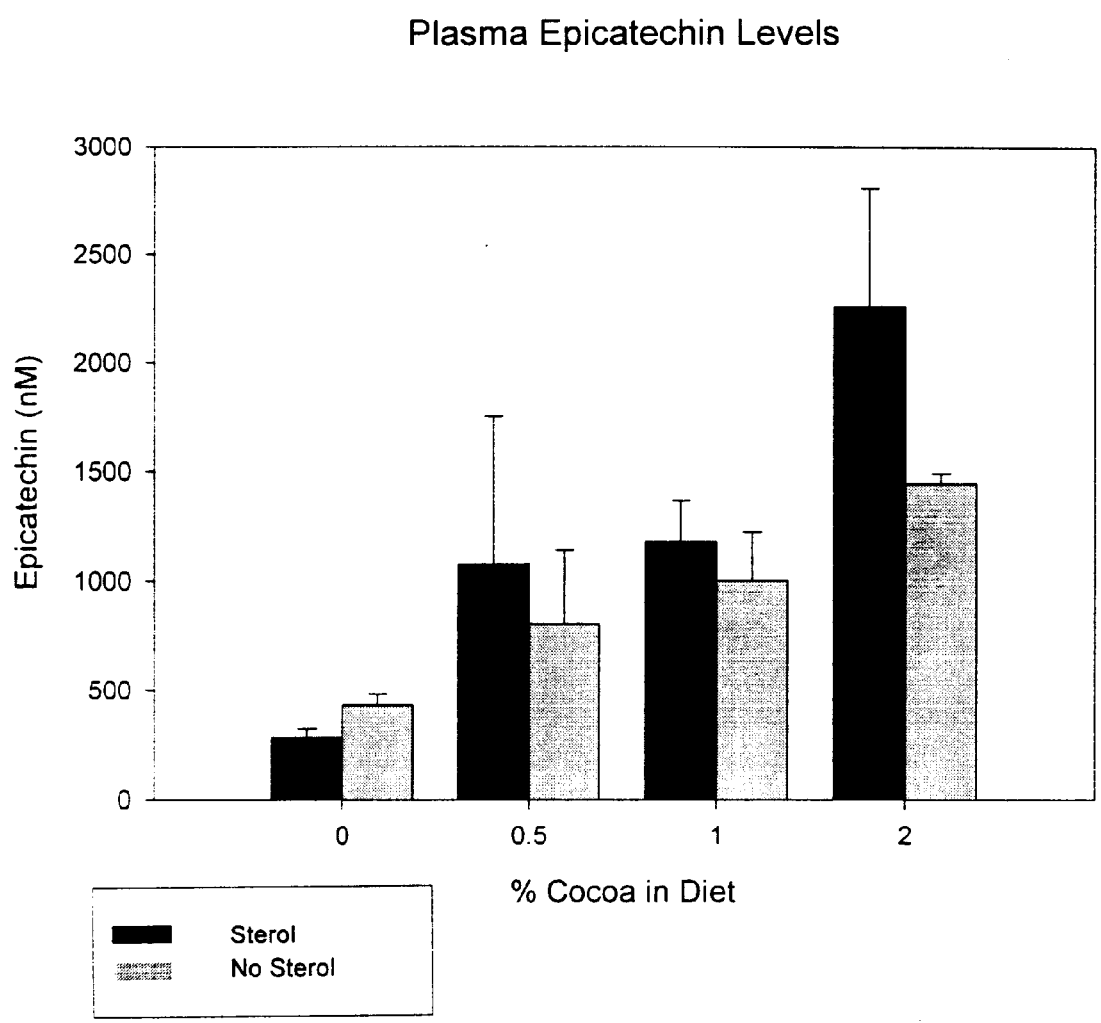
FIG. 6 shows the effects of the phytosterols, cocoa procyanidins and a combination thereof on the absorption of epicatechin into the blood plasma.

Referring to FIG. 6, the amount of the absorbed epicatechin increased in a dose dependent fashion. Surprisingly, the administration of phytosterols enhanced the absorption of epicatechin so that, for example, at 2 wt % CPd diet, the epicatechin plasma levels were enhanced by about 30% in comparison to the comparable diet without phytosterols. Hence, the phytosterol augmented the bioavailability of epicatechin.

Figure 7:
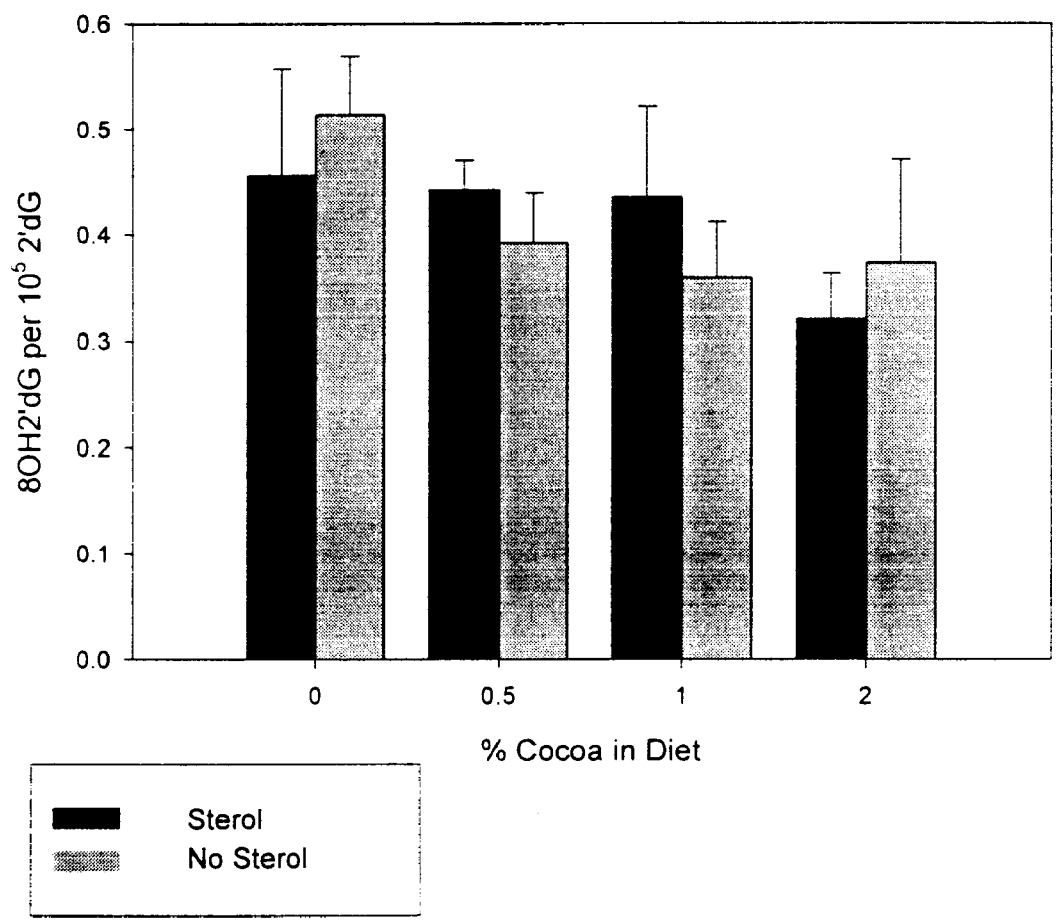
FIG. 7 shows the effects of the phytosterols, cocoa procyanidins and a combination thereof on the oxidative damage to DNA.

Referring to FIG. 7, CPd inhibited oxidative damage to DNA in a dose dependent manner. Surprisingly, at higher doses of CPd (2 wt %), an unexpected reduction in the oxidative damage to DNA was observed indicating a synergistic effect of phytosterols and CPd in preventing oxidative damage to DNA.

Figure 8:
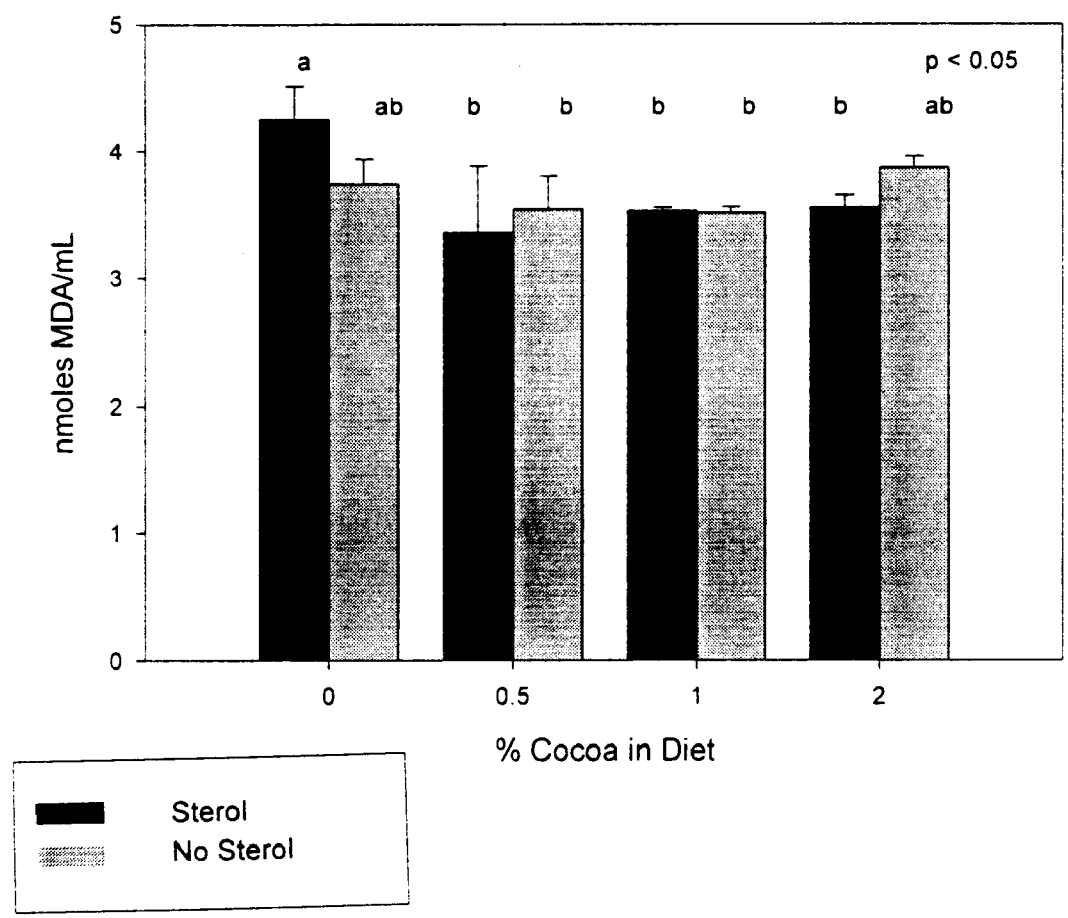
FIG. 8 shows the effects of the phytosterols, cocoa procyanidins and a combination thereof on the oxidative damage to lipids.

Referring to FIG. 8, feeding a diet containing phytosterols surprisingly caused a higher oxidative stress than the control diet, i.e., the intake of phytosterol together with food (without cocoa procyanidins), which was recommended in the art prior to the filing date of this application, exacerbated the oxidative stress. Feeding of cocoa procyanidins reversed or blunted this negative effect of phytosterols.

Total plasma cholesterol was also measured and the results are represented in Table 3.

TABLE 3

| Total Plasma Cholesterol | | |
|---|---|---|
| | Count | Mean |
| 2% Sterol | 3 | 84,000 |
| 2% Sterol + 0.5% Cocoa | 2 | 84,500 |
| 2% Sterol + 1% Cocoa | 3 | 82,000 |
| 2% Sterol + 2% Cocoa | 3 | 80,000 |
| No Sterol + No Cocoa | 3 | 88,333 |
| 0.5% Cocoa | 3 | 82,667 |
| 1% Cocoa | 3 | 87,000 |
| 2% Cocoa | 3 | 81,667 |

Referring to Table 3, as expected, phytosterols reduced cholesterol levels. Surprisingly, however, when phytosterols were administered with CPd, the cholesterol levels decreased even more, in a dose dependent manner. For example, the mean total cholesterol level of the three rats fed a phytosterol-containing diet was 84 mg/dl. Supplementation of this diet with 2 wt % CPd resulted in an additional decrease of total cholesterol to 80 mg/dl, indicating a synergistic effect of the two compounds. The rats fed the control diet had a mean cholesterol level of 88.3 mg/dl.

Example 6

Food Compositions Containing Cholesterol Lowering Agents in Combination with Cocoa Procyanidin Containing Cocoa or Chocolate Dark chocolate, toffee chew and granola bars containing cholesterol lowering agents were prepared.

Toffee chew was prepared from the ingredients shown in Table 4 by pre-blending sugar and cocoa and mixing it with caramel. Free phytosterols (as is or pulverized) were added to the sugar and cocoa mix.

TABLE 4

| Phytosterol-Containing Toffee Chews | | | | |
|---|---|---|---|---|
| | % Formula-range | % Formula | Phytosterols | Cocoa Procyanidins |
| Caramel | 55–65 | 63 | | |
| Cocoa | 20–30 | 22 | | |
| Sugar | 5–10 | 7.4 | | |
| Phytosterols | 5–12 | 7.5 | | |
| Total per 100 g | | | 7.5 | 550 |
| Total per 45 g serving | | | 3.375 | 248 |

Dark chocolate containing a free sterol was prepared using a commercially available dark chocolate (DOVE Dark available from Mars Inc.). To facilitate mixing with melted chocolate and to avoid any adverse effect on the chocolate texture, granulated forms of plant sterol/stanol were milled on Universal Muche M20, manufactured by IKA, for 30–60 seconds, mixed, and milled for another 30 seconds until the particle size became comparable to that of chocolate. Dark chocolate was melted and the sterol was added by slow mixing to ensure uniform distribution of sterol particles. The resulting composition is shown in Table 5.

TABLE 5

Phytosterol-Containing Dark Chocolate

|  | % Formula-range | % Formula | Phytosterols | Cocoa Procyanidins |
|---|---|---|---|---|
| Dark Chocolate | 88–95 | 92.5 | | |
| Phytosterols | 5–12 | 7.5 | | |
| Total per 100 g | | | 7.5 | 361 |
| Total per 45 g serving | | | 3.375 | 162 |

Granola bars containing a cholesterol lowering oat fiber was prepared from the ingredients listed in Tables 6 and 7. The syrup binder was prepared by melting palm kernel oil to 45 C. and was kept at that temperature until it was ready for use. Corn syrup, glycerin, cocoa powder, brown sugar, salt, lecithin, and propyl gallate were combined and the palm kernel oil added. The mixture was kept warm. To prepare granola, oats or soy puffs (available from Sovex Food, Collegedale, Tenn.) were blended with the chocolate pieces and the warm syrup binder prepared as described above was folded into the mixture. The granola mixture was then made into slabs, dusted with a mixture of 10× sugar (62%), cocoa powder (33%), and cinnamon (5%), and cut into pieces. The cocoa powder used in the mixture was prepared according to the method of U.S. Pat. No. 6,015,913 to Kealey et al.

TABLE 6

Granola Bar with Chocolate and Oats

|  | % Formula-range | % Formula | Oats | Cocoa Procyanidins |
|---|---|---|---|---|
| 63 DE Corn Syrup | 20–30 | 24.0 | | |
| Palm Kernel Oil | 0–4 | 3.2 | | |
| Glycerin | 2–3 | 2.4 | | |
| Cocoa Powder | 1–5 | 1.7 | | |
| Brownulated Sugar | 1–2 | 1.3 | | |
| Salt | 0.2–0.5 | 0.3 | | |
| Lecithin | 0.1–0.5 | 0.1 | | |
| Propyl Gallate | 0.01–0.05 | 0.01 | | |
| Oats | 20–35 | 30 | | |
| Sugar | 0–20 | 11 | | |
| Vegetable Oil | 0–10 | 6 | | |
| Semi-sweet chocolate pieces | 10–30 | 20 | | |
| Total per 100 g | | | 30 | 150 |
| Total per 45 g serving | | | 13.5 | 68 |

TABLE 7

Granola Bar with Chocolate and Soy Protein

|  | % Formula-range | % Formula | Soy Protein | Cocoa Procyanidins |
|---|---|---|---|---|
| 63 DE Corn Syrup | 20–30 | 24.0 | | |
| Palm Kernel Oil | 0–4 | 3.2 | | |
| Glycerin | 2–3 | 2.4 | | |
| Cocoa Powder | 1–5 | 1.7 | | |
| Brownulated Sugar | 1–2 | 1.3 | | |
| Salt | 0.2–0.5 | 0.3 | | |
| Lecithin | 0.1–0.5 | 0.1 | | |
| Propyl Gallate | 0.01–0.05 | 0.01 | | |
| Soy Pieces | 50–60 | 52 | | |
| Semi-sweet chocolate pieces | 10–30 | 15 | | |
| Total per 100 g | | | 20 | 125 |
| Total per 45 g serving | | | 9 | 56 |

What is claimed is:

1. A pharmaceutical, a dietary supplement or a food additive comprising an effective amount of a cocoa procyanidin monomer and/or oligomer and an effective amount of a sterol and/or stanol based cholesterol lowering agent.

2. The pharmaceutical, the dietary supplement or the food additive of claim 1, further comprising a soy protein, a soluble fiber and/or L-arginine.

3. The pharmaceutical, the dietary supplement or the food additive of claim 1 further comprising at least one component selected from the group consisting of:
calcium, potassium, magnesium, vitamin E, vitamin C, any of the vitamins of the B complex, a carotenoid, guar gum and a mono or poly unsaturated fatty acid.

4. The pharmaceutical, the dietary supplement or the food additive of claim 1, wherein the cocoa procyanidin monomer and/or oligomer is in the form of (i) a cocoa ingredient, (ii) a procyanidin containing cocoa extract, or (iii) a fraction of the cocoa extract containing at least one procyanidin monomer or oligomer.

5. A food other than a confectionery comprising an effective amount of a cocoa procyanidin monomer and/or oligomer and an effective amount of a sterol and/or stanol based cholesterol lowering agent.

6. The food of claim 5, further comprising a soy protein, a soluble fiber and/or L-arginine.

7. The food of claim 5, further comprising at least one component selected from the group consisting of:
calcium, potassium, magnesium, vitamin E, vitamin C, any of the vitamins of the B complex, a carotenoid, guar gum and a mono or poly unsaturated fatty acid.

8. The food of claim 5, wherein the cocoa procyanidin monomer and/or oligomer is in the form of (i) a cocoa ingredient, (ii) a procyanidin containing cocoa extract, or (iii) a fraction of the cocoa extract containing at least one procyanidin monomer or oligomer.

9. The food of claim 5, wherein the food is a beverage.

10. The food of claim 5, wherein the food is a pet food.

11. A cholesterol reducing confectionery comprising an effective amount of a cocoa procyanidin monomer and/or oligomer and an effective amount of a sterol and/or stanol based cholesterol lowering agent.

12. The confectionery of claim 11, further comprising a soy protein, a soluble fiber and/or L-arginine.

13. The confectionery of claim 11 further comprising at least one component selected from the group consisting of:
calcium, potassium, magnesium, vitamin E, vitamin C, any of the vitamins of the B complex, a carotenoid, guar gum, and a mono or polyunsaturated fatty acid.

14. The confectionery of claim 11, wherein the cocoa procyanidin monomer and/or oligomer is in the form of (i) a cocoa ingredient, (ii) a procyanidin containing cocoa extract, (iii) or a fraction of the cocoa extract containing at least one procyanidin monomer or oligomer.

15. The confectionery of claim 11, wherein said confectionery is selected from the group consisting of a chocolate, a chocolate covered candy, a baked product, and a granola bar.

16. The confectionery of claim 11, wherein said confectionery has at least one of the following properties:
inducing vasorelaxation, inhibiting lypoxygenase (LOX) activity, inhibiting oxidation of LDL, enhancing nitric oxide synthase (NOS) activity, increasing the level of nitric oxide (NO), inhibiting platelet aggregation, monocyte adhesion and proliferation of vascular smooth muscle, reducing blood pressure, reducing thrombosis, and modulating oxidative stress.

17. A cholesterol reducing chocolate comprising an effective amount of a cocoa procyanidin monomer and/or oligomer and an effective amount of a sterol and/or stanol based cholesterol lowering agent.

* * * * *